US012070459B2

(12) United States Patent
Li et al.

(10) Patent No.: US 12,070,459 B2
(45) Date of Patent: *Aug. 27, 2024

(54) PHARMACEUTICAL CAPSULE COMPOSITIONS COMPRISING LUMATEPERONE MONO-TOSYLATE

(71) Applicant: INTRA-CELLULAR THERAPIES, INC., New York, NY (US)

(72) Inventors: Peng Li, New Milford, NJ (US); Robert Davis, San Diego, CA (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,345

(22) Filed: Nov. 8, 2023

(65) Prior Publication Data

US 2024/0091224 A1   Mar. 21, 2024

Related U.S. Application Data

(63) Continuation of application No. 18/478,482, filed on Sep. 29, 2023, which is a continuation of application No. 17/582,516, filed on Jan. 24, 2022, now Pat. No. 11,806,348, which is a continuation of application No. 17/332,417, filed on May 27, 2021, now Pat. No. 11,690,842, which is a continuation of application No. 16/903,133, filed on Jun. 16, 2020, now Pat. No. 11,052,084, which is a continuation of application No. 16/557,083, filed on Aug. 30, 2019, now Pat. No. 10,695,345.

(60) Provisional application No. 62/725,948, filed on Aug. 31, 2018, provisional application No. 62/779,923, filed on Dec. 14, 2018.

(51) Int. Cl.
*A61K 31/4985* (2006.01)
*A61K 9/00* (2006.01)
*A61K 9/16* (2006.01)
*A61K 9/48* (2006.01)

(52) U.S. Cl.
CPC ........ *A61K 31/4985* (2013.01); *A61K 9/0053* (2013.01); *A61K 9/16* (2013.01); *A61K 9/4825* (2013.01); *A61K 9/485* (2013.01); *A61K 9/4858* (2013.01); *A61K 9/4891* (2013.01)

(58) Field of Classification Search
CPC ..... A61K 31/4985; A61K 9/48; A61K 9/0053
See application file for complete search history.

(56) References Cited

U.S. PATENT DOCUMENTS

| 2,490,813 | A | 12/1949 | Hughes et al. |
| 3,299,078 | A | 1/1967 | Pachter |
| 3,813,392 | A | 5/1974 | Sellstedt et al. |
| 3,914,421 | A | 10/1975 | Rajagopalan |
| 4,001,263 | A | 1/1977 | Plattner et al. |
| 4,115,577 | A | 9/1978 | Rajagopalan |
| 4,136,145 | A | 1/1979 | Fuchs et al. |
| 4,183,936 | A | 1/1980 | Rajagopalan |
| 4,219,550 | A | 8/1980 | Rajagopalan |
| 4,238,607 | A | 12/1980 | Rajagopalan |
| 4,389,330 | A | 6/1983 | Tice et al. |
| 4,522,944 | A | 6/1985 | Doria et al. |
| 4,530,840 | A | 7/1985 | Tice et al. |
| 4,849,246 | A | 7/1989 | Schmidt |
| 4,971,971 | A | 11/1990 | Tokunaga et al. |
| 4,985,432 | A | 1/1991 | Tokunaga et al. |
| 5,114,976 | A | 5/1992 | Norden |
| 5,151,419 | A | 9/1992 | Perenyi et al. |
| 5,538,739 | A | 7/1996 | Bodmer et al. |
| 5,576,460 | A | 11/1996 | Buchwald et al. |
| 5,629,003 | A | 5/1997 | Horstmann et al. |
| 5,648,539 | A | 7/1997 | Goodbrand |
| 5,648,542 | A | 7/1997 | Goodbrand et al. |
| 5,654,482 | A | 8/1997 | Goodbrand |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,763,476 | A | 6/1998 | Delbressine et al. |
| 5,834,493 | A | 11/1998 | Gil Quintero et al. |
| 5,847,166 | A | 12/1998 | Buchwald et al. |
| 5,902,901 | A | 5/1999 | Goodbrand et al. |
| 5,922,338 | A | 7/1999 | Erich et al. |
| 5,948,430 | A | 9/1999 | Zerbe et al. |
| 6,043,370 | A | 3/2000 | Kubo et al. |
| 6,166,226 | A | 12/2000 | Buchwald et al. |
| 6,221,335 | B1 | 4/2001 | Foster |
| 6,235,936 | B1 | 5/2001 | Buchwald et al. |

(Continued)

FOREIGN PATENT DOCUMENTS

| EP | 0 058 481 | 8/1982 |
| EP | 0 856 508 | 8/1998 |

(Continued)

OTHER PUBLICATIONS

Glube et al (Results in Pharma Sciences, 2013, vol. 3, pp. 1-6) (Year: 2013).*
"Study of a Novel Antipsychotic ITI-007 in Schizophrenia," Clinical Trials.gov, 6 pages, Dec. 26, 2011.
"Securities," Bennett v. Alkermes, Inc., at http://securities.stanford.edu/filings-documents/1029/ALKS03-01/20031029_r01c_0312091.pdf (retrieved from the internet on Jun. 13, 2017), (2003).
Alvir, et al., "Clozapine-Induced Agranulocytosis," *The New England Journal of Medicine*, vol. 329, No. 3, pp. 162-167, (1993).
Angst et al. "Prevalence and Characteristics of Undiagnosed Bipolar Disorders in Patients With a Major Depressive Episode", *Arch Gen Psychiatry*, vol. 68, No. 8, pp. 701-709, (2011).

(Continued)

*Primary Examiner* — Mark V Stevens
(74) *Attorney, Agent, or Firm* — Hoxie & Associates LLC

(57) ABSTRACT

The present disclosure relates to pharmaceutical capsules comprising lumateperone, in free, or pharmaceutically acceptable salt form, optionally in combination with one or more additional therapeutic agents, processes for manufacture thereof and methods of use in the treatment or prophylaxis of disease.

28 Claims, No Drawings

(56) References Cited

U.S. PATENT DOCUMENTS

| | | |
|---|---|---|
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,419,952 B2 | 7/2002 | Wong et al. |
| 6,440,710 B1 | 8/2002 | Keinan et al. |
| 6,448,243 B1 | 9/2002 | Kitazawa et al. |
| 6,465,693 B2 | 10/2002 | Buchwald et al. |
| 6,541,639 B2 | 4/2003 | Zhou et al. |
| 6,544,559 B2 | 4/2003 | Mesens et al. |
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,603,008 B1 | 8/2003 | Ando et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,828,314 B2 | 12/2004 | Frank et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,517,990 B2 | 4/2009 | Ito et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,414,922 B2 | 4/2013 | Bryson et al. |
| 8,461,148 B2 | 6/2013 | Hollander |
| 8,598,119 B2 | 12/2013 | Mates et al. |
| 8,603,514 B2 | 12/2013 | Yang et al. |
| 8,648,077 B2 | 2/2014 | Tomesch et al. |
| 8,652,378 B1 | 2/2014 | Yang et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,221,176 B2 | 3/2019 | Tomesch et al. |
| 10,245,260 B2 | 4/2019 | Yao et al. |
| 10,322,134 B2 | 6/2019 | Vanover et al. |
| 10,464,938 B2 | 11/2019 | Tomesch et al. |
| 10,472,359 B2 | 11/2019 | Li et al. |
| 10,597,395 B2 | 3/2020 | Tomesch et al. |
| 10,654,854 B2 | 5/2020 | Li et al. |
| 10,688,097 B2 | 6/2020 | Yao et al. |
| 10,702,522 B2 | 7/2020 | Mates et al. |
| 10,716,786 B2 | 7/2020 | Li et al. |
| 10,844,061 B2 | 11/2020 | Li et al. |
| 10,960,009 B2 | 3/2021 | Vanover et al. |
| 10,960,010 B2 | 3/2021 | Vanover et al. |
| 11,026,951 B2 | 6/2021 | Mates et al. |
| 11,053,245 B2 | 7/2021 | Mates et al. |
| 11,124,514 B2 | 9/2021 | Sharon et al. |
| 11,311,536 B2 | 4/2022 | Li |
| 11,331,316 B2 | 5/2022 | Li |
| 2001/0008942 A1 | 7/2001 | Buchwald et al. |
| 2001/0036472 A1 | 11/2001 | Wong et al. |
| 2002/0155154 A1 | 10/2002 | Wong et al. |
| 2003/0065187 A1 | 4/2003 | Buchwald et al. |
| 2004/0019216 A1 | 1/2004 | Buchwald et al. |
| 2004/0034015 A1 | 2/2004 | Robichaud et al. |
| 2004/0085699 A1 | 5/2004 | William |
| 2004/0092534 A1 | 5/2004 | Yam et al. |
| 2004/0122226 A1 | 6/2004 | Ghosh et al. |
| 2004/0127482 A1 | 7/2004 | Robichaud et al. |
| 2004/0138468 A1 | 7/2004 | Buchwald et al. |
| 2004/0142970 A1 | 7/2004 | Chung et al. |
| 2004/0180875 A1 | 9/2004 | Lee et al. |
| 2004/0209864 A1 | 10/2004 | Robichaud et al. |
| 2005/0058703 A1* | 3/2005 | Chang .................. A61K 9/4825 424/456 |
| 2005/0166771 A1 | 8/2005 | Gygi et al. |
| 2005/0215794 A1 | 9/2005 | Buchwald et al. |
| 2005/0222209 A1 | 10/2005 | Zeldis et al. |
| 2005/0248900 A1 | 11/2005 | Anthony |
| 2005/0250959 A1 | 11/2005 | Buchwald et al. |
| 2006/0178362 A1 | 8/2006 | Robichaud et al. |
| 2006/0205787 A1 | 9/2006 | Muller et al. |
| 2006/0264673 A1 | 11/2006 | Buchwald et al. |
| 2007/0049759 A1 | 3/2007 | Ghosh et al. |
| 2007/0066677 A1 | 3/2007 | Igo et al. |
| 2007/0082929 A1 | 4/2007 | Gant et al. |
| 2007/0197695 A1 | 8/2007 | Potyen et al. |
| 2007/0203120 A1 | 8/2007 | McDevitt et al. |
| 2008/0069885 A1 | 3/2008 | Mesens et al. |
| 2008/0132552 A1 | 6/2008 | Kleinman et al. |
| 2008/0194592 A1 | 8/2008 | Mates et al. |
| 2008/0249082 A1 | 10/2008 | Hollander |
| 2008/0280941 A1 | 11/2008 | Lourtie |
| 2008/0303137 A1 | 12/2008 | Ward et al. |
| 2009/0076159 A1 | 3/2009 | Czarnik |
| 2009/0209608 A1 | 8/2009 | Czarnik |
| 2010/0159033 A1 | 6/2010 | Gant et al. |
| 2011/0020369 A1 | 1/2011 | De Wall Malefyt et al. |
| 2011/0071080 A1 | 3/2011 | Mates et al. |
| 2011/0112105 A1* | 5/2011 | Tomesch ................ A61P 25/24 514/250 |
| 2011/0269777 A1 | 11/2011 | Bachurin et al. |
| 2012/0196814 A1 | 8/2012 | Gong et al. |
| 2013/0046097 A1 | 2/2013 | Tomesch et al. |
| 2013/0202692 A1 | 8/2013 | Mates et al. |
| 2014/0088083 A1 | 3/2014 | Hollander |
| 2014/0210117 A1 | 7/2014 | Friesen et al. |
| 2014/0323491 A1 | 10/2014 | Tomesch et al. |
| 2014/0364609 A1 | 12/2014 | Tomesch et al. |
| 2015/0004237 A1 | 1/2015 | Edgar et al. |
| 2015/0031804 A1 | 1/2015 | Shiramizu et al. |
| 2015/0038519 A1 | 2/2015 | Mates et al. |
| 2015/0072964 A1* | 3/2015 | Mates ..................... A61P 25/00 514/217 |
| 2015/0079172 A1 | 3/2015 | Mates et al. |
| 2015/0166540 A1* | 6/2015 | Mates ..................... A61P 25/20 514/250 |
| 2016/0031885 A1 | 2/2016 | Li et al. |
| 2016/0194326 A1 | 7/2016 | Tomesch et al. |
| 2016/0235720 A1 | 8/2016 | Foster et al. |

(56) References Cited

U.S. PATENT DOCUMENTS

| | | |
|---|---|---|
| 2016/0310502 A1 | 10/2016 | Vanover et al. |
| 2016/0354315 A1 | 12/2016 | Xiaoling |
| 2017/0037048 A1 | 2/2017 | Mates et al. |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0283417 A1 | 10/2017 | Li et al. |
| 2017/0319580 A1 | 11/2017 | Yao et al. |
| 2018/0044337 A1 | 2/2018 | Tomesch et al. |
| 2018/0092864 A1* | 4/2018 | Martin ............... A61P 25/08 |
| 2018/0200256 A1 | 7/2018 | Vanover et al. |
| 2019/0062334 A1 | 2/2019 | Mates et al. |
| 2019/0071445 A1 | 3/2019 | Li et al. |
| 2019/0218219 A1 | 7/2019 | Tomesch et al. |
| 2019/0231780 A1 | 8/2019 | Yao et al. |
| 2019/0290655 A1 | 9/2019 | Vanover et al. |
| 2019/0292185 A1 | 9/2019 | Tomesch et al. |
| 2019/0298730 A1 | 10/2019 | Vanover et al. |
| 2019/0328745 A1 | 10/2019 | Vanover et al. |
| 2019/0388418 A1 | 12/2019 | Li |
| 2020/0087305 A1 | 3/2020 | Tomesch et al. |
| 2020/0102304 A1 | 4/2020 | Li et al. |
| 2020/0102310 A1 | 4/2020 | Li et al. |
| 2020/0115380 A1 | 4/2020 | Tomesch et al. |
| 2020/0148683 A1 | 5/2020 | Peddy et al. |
| 2020/0157100 A1 | 5/2020 | Li |
| 2020/0392135 A1 | 12/2020 | Wennogle et al. |
| 2020/0407362 A1 | 12/2020 | Mates et al. |
| 2021/0002280 A1 | 1/2021 | Mates et al. |
| 2021/0032247 A1 | 2/2021 | Li et al. |

FOREIGN PATENT DOCUMENTS

| | | | |
|---|---|---|---|
| EP | 0 976 732 | 2/2000 | |
| EP | 1 245 553 | 10/2002 | |
| EP | 1 254 884 | 11/2002 | |
| EP | 1 539 115 | 6/2005 | |
| EP | 1 564 671 | 8/2005 | |
| GB | 1476087 | 6/1977 | |
| GB | 2145422 | 3/1985 | |
| RU | 2465267 | 10/2012 | |
| WO | WO 1995/013814 | 5/1995 | |
| WO | WO 1999/043643 | 9/1999 | |
| WO | WO 2000/002887 | 1/2000 | |
| WO | WO 2000/064899 | 11/2000 | |
| WO | WO 2002/059129 | 8/2002 | |
| WO | WO 2003/014118 | 2/2003 | |
| WO | WO 2005/030214 | 4/2005 | |
| WO | WO 2014/110322 | 7/2014 | |
| WO | WO 2017/117514 | 7/2017 | |
| WO | WO 2017/132408 | 8/2017 | |
| WO | WO 2018/106916 | 6/2018 | |
| WO | WO 2018/175969 | 9/2018 | |
| WO | WO-2018189646 A1 * | 10/2018 | ........... A61K 31/519 |
| WO | WO 2019/102240 | 5/2019 | |

OTHER PUBLICATIONS

Avendano, et al., "The problem of the existence of C(Ar)-H . . . N Intramolecular Hydrogen Bonds in a Family of 9-Azaphenyl-9H-carbazoles," *J. Chem. Soc. Perkin Trans.*, vol. 2, pp. 1547-1555, (1993).

Baille, T.A., "The Use of Stable Isotopes in Pharmacological Research," *Pharmacol. Reviews*, vol. 33, No. 2, pp. 81-132, (1981).

Barman et al., "Newer antipsychotics: Brexpiprazole, cariprazine, and lumateperone: A pledge or another unkept promise?", *World J. Psychiatr.*, 11(12): 1228-38 (2021).

Beletskaya, et al., "Pd- and Cu-catalyzed selective arylation of benzotriazole," Tetrahedron Letters, vol. 39, pp. 5617-5620, (1998).

Bennett, et al., "Cecil Textbook of Medicine," 20th Edition, vol. 1, pp. 1004-1010, (1996).

Berger, et al., "Synthesis of Some Conformationally Restricted Analogs of Fentanyl," Journal of Medicinal Chemistry, vol. 20, No. 4, pp. 600-602, (1977).

Boger, et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5,8-quinone Ring System," J. Org. Chem., vol. 50, pp. 5782-5789, (1985).

Borghans et al., "Animal Models for Posttraumatic Stress Disorder: An Overview of What is Used in Research," *World J. Psychiatr.*, vol. 5, No. 4, pp. 387-396, (2015); DOI: 10.5498/wjp.v5.i4.387.

Bowman, et al., "Intramolecular Aromatic Substitution (SRN1) Reactions—Use of Entrainment for the Preparation of Benzothiazoles," Tetrahedron Letters, vol. 23, pp. 5093-5096, (1982).

Bowman, et al., "Copper (1) Catalysed Aromatic Nucleophilic Substitution: A Mechanistic and Synthetic Comparison with the SRN 1 Reaction," Tetrahedron Letters, vol. 25, No. 50, pp. 5821-5824, (1984).

Bowman, et al.,"Synthesis of 1H-quinazoline-4-ones Using Intramolecular Aromatic Nucelophilic Substitution," ARKIVOC, vol. x, pp. 434-442 (2003).

Bremner, et al., "Neuroimaging of Posttraumatic Stress Disorder", Psychiatric Annals Journal, vol. 28, No. 8, p. 445-450, (1998).

Browne, T.R., "Stable Isotope Techniques in Early Drug Development: An Economic Evaluation," J. Clin. Pharmacol., vol. 38, pp. 213-220, (1998).

Bryan-Lluka, et al., "Potencies of Haloperidol Metabolites as Inhibitors of the Human Noradrenaline, Dopamine and Serotonin Transporters in Transfected COS-7 Cells," Naunyn-Shemiedeberg's Arch Pharmacol, vol. 360, pp. 109-115, (1999).

Byrn, et al., "Pharmaceutical Solids: A Strategic Approach to Regulatory Considerations," Pharmaceutical Research, vol. 12, No. 7, pp. 945-954, (1995).

Caira, M.R., "Crystalline Polymorphism of Organic Compounds," Topics in Current Chemistry, vol. 198, p. 163-203, (1998).

Cherrah, et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, pp. 653-657, (1987).

Correll et al., "Efficacy and Safety of Lumateperone for Treatment of Schizophrenia A Randomized Clinical Trial", *JAMA Psychiatry*, 77(4): 349-358 (2020).

Crawford, et al., "Copper-Catalyzed Amidations of Bromo Substituted Furans and Thiophenes," Tetrahedron Letters, vol. 43, pp. 7365-7368, (2002).

Darmani, et al., "Do Functional Relationships Exist Between 5-HT1A and 5-HT2 Receptors?" Pharmacology and Biochemistry & Behavior, vol. 36, pp. 901-906, (1990).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis, et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.

Davis, et al., "ITI-007 in the Treatment of Schizophrenia: From Novel Pharmacology to Clinical Outcomes," Expert Review of Neurotherapeutics, vol. 16, No. 6, pp. 601-614, (2016).

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93.

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Dhawan et al., "Sleep-related Problems of Parkinson's Disease," *Age and Ageing*, vol. 35, pp. 220-228, (2006); DOI: 10.1093/ageing/afj087.

(56) References Cited

OTHER PUBLICATIONS

Dyck, et al., "Effects of Deuterium Substitution on the Catabolism of β-Phenylethylamine: An In Vivo Study," Journal of Neurochemistry, vol. 46, Issue 2, pp. 399-404, (1986).
Edinoff et al., "Lumateperone for the Treatment of Schizophrenia", *Psychopharmacology Bulletin*, 50(4): 32-59 (2020).
Evindar, et al., "Copper- and Palladium-Catalyzed Intramolecular Aryl Guanidinylation: An Efficient Method for the Synthesis of 2-Aminobenzimidazoles", Organic Letters, vol. 5, No. 2, pp. 133-136, (2003).
Ezquerra, et al., "Efficient Reagents for the Synthesis of 5-, 7-, and 5, 7-Substitued Indoles Starting from Aromatic Amines: Scope and Limitations", J. Org. Chem., vol. 61, pp. 5804-5812, (1996).
Fawcett, J., "Posttraumatic Stress Disorder, Stress, and Happiness", Psychiatric Annals Journal, vol. 28, No. 8, pp. 427-428, (1998).
Fee, et al., "Copper (II)-Promoted Solvolyses of Nickel (II) Complexes III. Tetradentate Schiff Base Ligands Containing Various Diamine Segments," Aust. J. Chem., vol. 26, pp. 1475-1485, (1973).
Ferreira, et al., "Novel Synthetic Routes to Thienocarbazoles Via Palladium or Copper Catalyzed Amination or Amidation of Arylhalides and Intramolecular Cyclization", Tetrahedron, vol. 58, pp. 7943-7949, (2002).
Finet, et al., "Recent Advances in Ullmann Reaction: Copper (II) Diacetate Catalysed N-, )- and S-arylation Involving Polycoordinate Heteroatomic Derivatives," Current Organic Chemistry, vol. 6, pp. 597-626, (2002).
Fletcher et al., "Perceiving is Believing: A Bayesian Approach to Explaining the Positive Symptoms of Schizophrenia," *Nature Reviews/Neuroscience*, vol. 10, pp. 48-58, (2009).
Foster, A.B., "Deuterium Isotope Effects in the Metabolism of Drugs and Xenobiotics: Implications for Drug Design," Advances in Drug Research, vol. 14, pp. 1-40, (1985).
Foster, et al., "Acetylcholinesterase Inhibitors Reduce Spreading Activation in Dementia," Neuropsychologia, vol. 50, pp. 2093-2099, (2012).
Foster et al., "Emerging Approaches for Treatment of Schizophrenia: Modulation of Cholinergic Signaling", *Discov. Med.*, 14(79): 413-420 (2012).
Friedman, M.J.., "Current and Future Drug Treatment for Posttraumatic Stress Disorder Patients", Psychiatric Annals Journal, vol. 28, No. 8, pp. 464-468, (1998).
Goodbrand, et al., "Ligand-Accelerated Catalysis of the Ullmann Condensation: Application to Hole Conducting Triarylamines," J. Org. Chem., vol. 64, pp. 670-674, (1999).
Gouyette, A., "Synthesis of Deuterium-labelled Elliptinium and its Use in Metabolic Studies," Biomedical and Environmental Mass Spectrometry, vol. 15, pp. 243-247, (1988).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Hackam, et al., "Translation of Research Evidence from Animals to Humans," JAMA, vol. 296, No. 14, pp. 1731-1732, (2006).
Hamann, et al., "Systematic Variation of Bidentate Ligands Used in Aryl Halide Amination. Unexpected Effects of Steric, Electronic, and Geometric Perturbations", J. Am. Chem. Soc., vol. 120, pp. 3694-3703, (1998).
Harbert, et al., "Neuroleptic Activity in 5-Aryltetrahydro-y-carbolines", J. Med. Chem., vol. 23, pp. 635-643, (1980).
Hartwig, J., "Palladium-Catalyzed Amination of Aryl Halides: Mechanism and Rational Catalyst Design," Synlett, pp. 329-340, (1996).
Harvey, et al., "Serotonin and Stress: Protective or Malevolent Actions in the Biobehavioral Response to Repeated Trauma?," Annals of the New York Academy of Sciences, vol. 1032, pp. 267-272, (2004); DOI: 10.1196/annals.1314.035.
Haskins, N.J., "The Application of Stable Isotopes in Biomedical Research," Biological Mass Spectrometry, vol. 9, No. 7, pp. 269-277, (1982).
Hassan, et al., "Aryl-aryl Bond Formation One Century After the Discovery of the Ullmann Reaction," Chem. Rev., vol. 102, pp. 1359-1469, (2002).
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Honma, S., et al., "The Metabolism of Roxatidine Acetate Hydrochloride: Liberation of Deuterium from the Piperidine Ring during Hydroxylation," Drug Metabolism and Disposition, vol. 15, No. 4, pp. 551, (1987).
Howes et al., "Glutamate and dopamine in schizophrenia: An update for the 21st century", J. Psychopharmacol., 29(2): 97-115 (2015).
Howland, R.H., "Deuterated Drugs," Journal of Psychosocial Nursing and Mental Health Services, 53(9): 13-16 (2015).
International Preliminary Report on Patentability for International Application No. PCT/US2013/036514 issued Oct. 14, 2014.
International Search Report issued in International Application No. PCT/US2008/003340, mailed Aug. 8, 2008, 3 pages.
International Search Report issued in International Application No. PCT/US2009/001608, mailed Apr. 27, 2009, 3 pages.
International Search Report issued in International Application No. PCT/US2009/003261, mailed Jul. 16, 2009.
International Search Report issued in International Application No. PCT/US2011/00719, mailed Jul. 5, 2011, 3 pages.
International Search Report issued in International Application No. PCT/US2013/036515, mailed Aug. 13, 2013, 3 pages.
International Search Report issued in International Application No. PCT/US2013/036514, mailed Aug. 16, 2013, 3 pages.
International Search Report issued in International Application No. PCT/US2013/036512, mailed Aug. 19, 2013, 4 pages.
International Search Report issued in International Application No. PCT/US2015/024340, mailed Jun. 25, 2015, 2 pages.
International Search Report issued in International Application No. PCT/US2015/024345, mailed Jun. 25, 2015, 3 pages.
International Search Report issued in International Application No. PCT/US2017/054962, date mailed Nov. 27, 2017, 3 pages.
Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).
Ito, et al., "Studies of Organic Catalytic Reactions. VI. The Function of Pyridine and Copper in the Rosenmund-von Braun Reaction," Bulletin of the Chemical Society of Japan, vol. 41, pp. 419-423, (1968).
Izrayelit, L., "Schizoaffective Disorder and PTSD Successfully Treated With Olanzapine and Supportive Psychotherapy", Psychiatric Annals Journal, vol. 28, No. 8, pp. 424-426, (1998).
Ji, et al., "Selective Amination of Polyhalopyridines Catalyzed by a Palladium-xantphos Complex," Organic Letters, vol. 5, No. 24, pp. 4611-4614, (2003).
Juorio, A.V., et al., "Effects of Acute and Chronic Phenelzine on Regional Monoamine Metabolism in Rats and its Potentiation by Deuterium Substitution," Naunyn-Schmiedeberg's Archives of Pharmacology, vol. 333, No. 3, pp. 240-245, (1986); Abstract only.
Kahn et al., "Residual Symptoms of Schizophrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kametani, et al., "A Novel Synthesis of Indole Derivatives," Heterocycles, vol. 14 No. 3, pp. 277-280, (1980).
Kang, et al., "Copper-catalyzed N-arylation of Aryl Iodides with Benzamides or Nitrogen Heterocycles in the Presence of Ethylendiamine," Synlett, No. 3, pp. 427-430, (2002).
Kay, et al., "The Positive and Negative Syndrome Scale (PANSS) for Schizophrenia," Schizophrenia Bulletin, vol. 13, No. 2, pp. 261-276, (1987).
Kendrick, "The newer, 'atypical' antipsychotic drugs—their development and current therapeutic use", *British J. General Practice*, 49: 745-749 (1999).
Kessler, et al., "Lifetime Prevalence and Age-of-Onset Distributions of DSM-IV Disorders in the National Comorbidity Survey Replication," Arch Gen Psychiatry, vol. 62, pp. 593-602, (2005).

(56) References Cited

OTHER PUBLICATIONS

Khorana, et al., "Gamma-Carbolines: Binding at 5-HT5A Serotonin Receptors," Bioorganic & Medicinal Chemistry, vol. 11, pp. 717-722, p. 718 Table 1, (2003).
Kiyomori, et al., "An Efficient Copper-catalyzed Coupling of Aryl Halides with Imidazoles," Tetrahedron Letters, vol. 40, pp. 2657-2660, (1999).
Klapars, et al., "A General and Efficient Copper Catalyst for the Amidation of Aryl Halides and the N-arylation of Nitrogen Heterocycles," J. Am. Chem. Soc., vol. 123, pp. 7727-7729, (2001).
Klapars, et al., "A General and Efficient Copper Catalyst for the Amidation of Aryl Halides," J. Am. Chem. Soc., vol. 124, pp. 7421-7428, (2002).
Kondratov, et al., "Nucelophilic Substitution in the Aromatic Series. Lv. Reaction of o-nitrochlorobenzene with Ammonia in the Presence of Copper Compounds," Zhurnal Organidreskoi Khimii, vol. 51, No. 11, pp. 2387-2390, (1979).
Koppel, et al., "Optimal Treatment of Alzheimer's Disease Psychosis: Challenges and Solutions," Neuropsychiatric Disease and Treatment, vol. 10, pp. 2253-2262, (2014).
Korczak et al., "Use of selective serotonin reuptake inhibitor medications for the treatment of child and adolescent mental illness", *Canadian Pediatric Society*, 18(9), pp. 487-491, https://cps.ca/en/documents/position/ use-of-SSR1s-for-child-adolescent-mental-illness, (2013).
Kwong, et al., "Mild and Efficient Copper-catalyzed Amination of Aryl Bromides with Primary Alkylamines," Organic Letters, vol. 5, No. 6, pp. 793-796, (2003).
Lebert, et al., "Trazodone in Fronto-Temporal Dementia," Research and Practice in Alzheimer's Disease, vol. 11, pp. 356-360, (2006).
Lee, et al. "Novel, Highly Potent, Selective 5-HT2A/D2 Receptor Antagonists as Potential Atypical Antipsychotics," Bioorg. Med. Chem. Lett., vol. 13, pp. 767-770, (2003).
Li, et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, vol. 57, pp. 2670-2682, (2014).
Lieberman, et al., "ITI-007 for the Treatment of Schizophrenia: A 4-Week Randomized, Double-Blind, Controlled Trial," Biol. Psychiatry, vol. 79, No. 12, pp. 952-961, (2015).
Lin, et al., "Dosage and Duration of Antipsychotic Treatment in Demented Outpatients with Agitation or Psychosis," Journal of the Formosan Medical Association, vol. 114, pp. 147-153, (2015).
Lipschitz, et al., "Childhood Posttraumatic Stress Disorder: A Review of Neurobiologic Sequelae," Psychiatric Annals Journal, vol. 28, No. 8, pp. 452-457, (1998).
Liriano et al., "Ketamine as treatment for post-traumatic stress disorder: a review." Drugs in Context, vol. 8, 7 pages (2019).
Lopez, et al., "Psychiatric Symptoms Vary with the Severity of Dementia in Probably Alzheimer's Disease," J. Neuropsychiatry Clin. Neurosc., vol. 15, No. 3, pp. 346-353, (2003).
Louie, et al., "Palladium-Catalyzed Synthesis of Arylamines from Aryl Halides, Mechanistic Studies lead to Coupling in the Absence of Tin Reagents," Tetrahedron Letters, vol. 36, No. 21, pp. 3609-3612, (1995).
Lounkine, et al., "Formal Concept Analysis for the Identification of Molecular Fragment Combinations Specific for Active and Highly Potent Compounds," J. Med. Chem., vol. 51, No. 17, pp. 5342-5348, (2008).
Madhusoodanan, et al., "Pharmacological Management of Behavioral Symptoms Associated with Dementia," World J. Psychiatr., vol. 4, No. 4, pp. 72-79, (2014).
Makadia et al., "Poly Lactic-co-Glycolic Acid (PLGA) as Biodegradable Controlled Drug Delivery Carrier," *Polymers (Basel)*, vol. 3, No. 3, pp. 1377-1397, (2011).
March, et al, Advanced Organic Chemistry; Reactions, Mechanisms and Structures, Fourth Edition, pp. 910-911, (1992).
Marcoux, et al., "A General Copper-catalyzed Synthesis of Diaryl Ethers," J. Am. Chem. Soc., vol. 119, pp. 10539-10540, (1997).
Marek et al., "Synergistic Action of 5-HT2A Antagonists and Selective Serotonin Reuptake Inhibitors in Neuropsychiatric Disorders", *Neuropsychopharmacology*, vol. 28, pp. 402-412, (2002).
Marek et al. Synergistic Action of 5-HT2A Antagonists and Selective Serotonin Reuptake Inhibitors in Neuropsychiatric Disorders. Neuropsychopharmacology, 2003. Vol. 28, pp. 402-412. (Year: 2003).
McConnell & AW Basit, "Modified-Release Oral Drug Delivery", *Aulton's Pharmaceutics*, Chap. 31, pp. 550-565 (2013).
Mohamed, et al., "Pharmacotherapy of PTSD in the U.S. Department of Veterans Affairs: Diagnostic- and Symptom-guided Drug Selection," J. Clin. Psychiatry, vol. 69, pp. 959-965, (2008).
Morgan, et al., "Acoustic Startle in Individuals With Posttraumatic Stress Disorder," Psychiatric Annals Journal, vol. 28, Issue 8, pp. 430-434, (1998).
Müller et al., "Detection of Depression in Acute Schizophrenia: Sensitivity and Specificity of 2 Standard Observer Rating Scales," *Can J Psychiatry*, vol. 51, No. 6, pp. 387-392, (2006).
Mulrooney, et al., "Recent Developments in Copper-catalyzed N-Arylation with Aryl Halides," Essay—University of Pennsylvania, (2004).
Murakami, et al., "Fischer Indolization of Ethyl Pyruvate 2-[2-(Trifluoromethyl) phenyl]-phenylhydrazone and New Insight into the Mechanism of the Goldberg Reaction," Chem. Pharm. Bull, vol. 43, No. 8, pp. 1281-1286, (1995).
Nagai, et al., "Synthesis of 2,3,4,4a,5,9b-hexahydro-1H-pyrido[4,3-b] indole Derivatives and Their Central Nervous System Activities," Journal of Medicinal Chemistry, vol. 22, No. 6, pp. 677-683, (1979).
Nihon rounen igaku zasshi, vol. 48, No. 3, pp. 195-204, (2011 nen). Partial English translation only, 2 pages.
Noble et al., "The Opioid Receptors as Targets for Drug Abuse Medication," *British Journal of Pharmacology*, vol. 172, pp. 3964-3979, (2015); DOI: 10.1111/bph.13190.
O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, pp. 388-400, (2011).
Perlis et al., "Clinical Features of Bipolar Depression Versus Major Depressive Disorder in Large Multicenter Trials", *Am J Psychiatry*, vol. 163, vol. 2, p. 225-231, (2006).
Pieniaszek, et al., "Moricizine Bioavailability via Simultaneous Dual, Stable Isotope Administration: Bioequivalence Implications," J. Clin. Pharmacol., vol. 39, pp. 817-825, (1999).
Pine et al., "Dopamine, Time, and Impulsivity in Humans," *The Journal of Neuroscience*, vol. 30, No. 26, pp. 8888-8896, (2010).
Pond, et al., "Stereospecific Reduction of Haloperidol in Human Tissues," Biochemical Pharmacology, vol. 44, No. 5, pp. 867-871, (1992).
Press Release, "Intra-Cellular Therapies Announces Additional Results from Phase I/II Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
"Protection for the Amino Group," Protective Groups in Organic Synthesis, Third Edition, John Wiley & Sons, Inc., pp. 494-505, (1999).
Rackova, et al., "Free Radical Scavenging and Antioxidant Activities of Substituted Hexahydropyridoindoles. Quantitative Structure-Activity Relationships." Journal of Medicinal Chemistry, vol. 49, No. 8, pp. 2543-2548, (2006).
Rainer, M.K., "Risperidone Long-acting Injection: A Review of its Long Term Safety and Efficacy," Neuropsychiatric Disease and Treatment, vol. 4, No. 5, pp. 919-927, (2008).
Ramaswamy et al., "Failed Efficacy of Ziprasidone in the Treatment of Post-Traumatic Stress Disorder," *Contemporary Clinical Trials Communications*, vol. 2, pp. 1-5, (2016).

(56) References Cited

OTHER PUBLICATIONS

Reynolds et al., "Longitudinal Change in Memory Performance Associated with HTR2A Polymorphism," *Neurobiology of Aging*, vol. 27, pp. 150-154, (2006).
Rye (Sleep Disorders and Parkinson's Disease, 2000, accessed online http://www.waparkinsons.org/edu_research/articles/Sleep_Disorders.html), 2 pages.
Sadighi, et al., "A Highly Active Palladium Catalyst System for the Arylation of Anilines," Tetrahedron Letters, vol. 39, pp. 5327-5330, (1998).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Schennach et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.
Seishinkei Shi, vol. 110, No. 7, pp. 557-584, (2008). Partial English translation only.
Semla et al., "Off-Label Prescribing of Second-Generation Antipsychotics to Elderly Veterans with Posttraumatic Stress Disorder and Dementia," *J. Am. Geriatr. Soc.*, vol. 65, No. 8, pp. 1789-1795, (2017); DOI: 10.1111/jgs.14897.
Sigel, et al., "Tenary Complexes in Solution," Inorganic Chemistry, vol. 13, No. 2, pp. 462-465, (1974).
Singhal, et al., "Drug Polymorphism and Dosage Form Design: A Practical Perspective," Advanced Drug Delivery Reviews, vol. 56, pp. 335-347, (2004).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.
Southwick, et al., "Neuroendocrine Alterations in Posttraumatic Stress Disorder," Psychiatric Annals Journal, vol. 28, No. 8, pp. 436-442, (1998).
Sugahara, et al., "A Facile Copper-Catalyzed Ullman Condensation: N-Arylation of Heterocyclic Compounds Containing an—NHCO—Moiety," Chem. Pharm. Bull., vol. 45, No. 4, pp. 719-721, (1997).
Suzuki et al., "Comparison of Nicotinamide, Ethyluirea and Polyethylene Glycol as Carriers for Nifedipine Solid Dirperssion Systems." *Chemical and Pharmaceutical Bulletin*, vol. 45, No. 10, pp. 1688-1693, (1997).
Taragano, et al., "A Double-Blind, Randomized, Fixed-Dose Trial of Fluoxetine vs. Amitriptyline in the Treatment of Major Depression Complicating Alzheimer's Disease," Psychosomatics, vol. 38, No. 3, pp. 246-252, (1997).
Tariot, et al., "Memantine Treatment in Patients with Moderate to Severe Alzheimer Disease Already Receiving Donepezil: A Randomized Controlled Trail," JAMA, vol. 291, No. 3, pp. 317-324, (2004).
Timmins, G.S., "Deuterated drugs: where are we now?" Expert Opinion on Therapeutic Patents, 1-9 (2014).
Tonn, et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes," Biological Mass Spectrometry, vol. 22, pp. 633-642, (1993).
Tung, R., "The Development of Deuterium-Containing Drugs," Innovations in Pharmaceutical Technology, vol. 32, pp. 1-4, (2010).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, et al., "Dopamine D2 receptor occupancy of lumateperone (ITI-007): a Positron Emission Tomography Study in patients with schizophrenia," Neuropsychopharmacology 44:598-605, (2019).
Vanover, K., et al., "ITI-007: A Novel Therapy for the Treatment of Schizophrenia and Related Psychoses," International Clinical Psychoparamcology, vol. 26, e56, 1 page, (2011).
Vanover et al., Abstracts of the 13th International Congress on Schizophrenia (ICOSR) (Apr. 2-6, 2011), *Schizophrenia Bull.* 37 Suppl. 1., p. 325 (Mar. 2011).
Vloeberghs et al., "Altered Circadian Locomotor Activity in APP23 Mice: A Model for BPSD Disturbances," *European Journal of Neuroscience*, vol. 20, pp. 2757-2766, (2004); DOI: 10.1111/j.1460-9568.2004.03755.x.
Vyas et al., "An Evaluation of Lumateperone Tosylate for the Treatment of Schizophrenia," *Expert Opinion on Pharmacotherapy*, vol. 21, No. 2, pp. 139-145, (2020); https://doi.org/10.1080/14656566.2019.1695778.
Wagaw, et al., "A Palladium-Catalyzed Method for the Preparation of Indoles Via the Fischer Indole Synthesis," Journal of the American Chemical Society, vol. 121, No. 44, pp. 10251-10263, (1999).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Weschules, et al., "Acetylcholinesterase Inhibitor and N-Methyl-D-Aspartic Acid Receptor Antagonist Use among Hospice Enrollees with a Primary Diagnosis of Dementia," Journal of Palliative Medicine, vol. 11, No. 5, pp. 738-745, (2008).
Wiese, M., "DSC Detection of Polymorphism in Pharmaceutical Anhydrous Dexamethasone Acetate," TA Instruments, TA 302, pp. 1-4, (2002).
Wolen, R. L., "The Application of Stable Isotopes to Studies of Drug Bioavailability and Bioequivalence," J. Clin. Pharmacol., vol. 26, pp. 419-424, (1986).
Wolfe, et al., "An Improved Catalyst System for Aromatic Carbon-nitrogen Bond Formation: The Possible Involvement of Bis(Phosphine) Palladium Complexes as Key Intermediates," J. Am. Chem. Soc., vol. 118, pp. 7215-7216, (1996).
Wolfe, et al., "Intramolecular Palladium-Catalyzed Aryl Amination and Aryl Amidation," Tetrahedron, vol. 52, No. 21, pp. 7525-7546, (1996).
Wolter, et al., "Synthesis of N-Aryl Hydrazides by Copper-Catalyzed Coupling of Hydrazides with Aryl Iodides," Organic Letters, vol. 3, No. 23, pp. 3803-3805, (2001).
Written Opinion of the International Searching Authority for International Application No. PCT/US2013/036514 mailed Aug. 16, 2013, 4 pages.
Written Opinion of the International Searching Authority for International Application No. PCT/US2017/054962 mailed Nov. 27, 2017, 8 pages.
Written Opinion of the International Searching Authority for International Application No. PCT/US2019/049062 mailed Nov. 15, 2019, 5 pages.
Yamada, et al., "A Mild Copper-mediated Intramolecular Amination of Aryl Halides," Synlett, No. 2, pp. 231-234, (2002).
Yang, et al., "The Development of Efficient Protocols for the Palladium-catalyzed Cyclization Reactions of Secondary Amides and Carbamates," Organic Letters, vol. 1, No. 1, pp. 35-37, (1999).
Yudofsky, et al., "Propranolol in the Treatment of Rage and Violent Behavior in Patients with Chronic Brain Syndromes," Am. J. Psychiatry, vol. 138, No. 2, pp. 218-220, (1981).
Zhang, et al., "Highly Efficient Copper-catalyzed N-arylation of Alkylamines with Aryl Iodides Using Phosphoramidite as Ligand," Catalysis Communications, vol. 6, pp. 784-787, (2005).
Zhang et al., "The Role of Serotonin 5-$HT_{2A}$ Receptors in Memory and Cognition," *Front. Pharmacol.*, vol. 6, No. 225, pp. 1-17, (2015); DOI: 10.3389/fphar.2015.00225.

* cited by examiner

PHARMACEUTICAL CAPSULE COMPOSITIONS COMPRISING LUMATEPERONE MONO-TOSYLATE

CROSS-REFERENCE TO RELATED APPLICATIONS

This patent application is a continuation of U.S. patent application Ser. No. 18/478,482, filed on Sep. 29, 2023, which is a continuation application of U.S. patent application Ser. No. 17/582,516, filed on Jan. 24, 2022, which is a continuation application of U.S. patent application Ser. No. 17/332,417, filed on May 27, 2021, which is a continuation application of U.S. patent application Ser. No. 16/903,133, filed on Jun. 16, 2020, which is a continuation of U.S. patent application Ser. No. 16/557,083, filed on Aug. 30, 2019, which claims priority to, and the benefit of, U.S. Provisional Application No. 62/725,948, filed on Aug. 31, 2018, and U.S. Provisional Application No. 62/779,923, filed on Dec. 14, 2018, the contents of each of which are hereby incorporated by reference in their entireties.

TECHNICAL FIELD

The present disclosure relates to pharmaceutical capsules comprising lumateperone, in free, or pharmaceutically acceptable salt form, optionally in combination with one or more additional therapeutic agents, processes for manufacture thereof and methods of use in the treatment or prophylaxis of disease.

BACKGROUND OF THE INVENTION

The substituted heterocycle fused gamma-carbolines lumateperone (4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone) is known to be a serotonin receptor (5-$HT_{2A}$), dopamine receptor (D1 and/or D2), and serotonin transporter (SERT) ligand, which is useful in treating a variety of central nervous system disorders.

Lumateperone antagonizes the serotonin-2A (5-$HT_{2A}$) receptor, and/or modulates dopamine receptor signaling at the level of key intra-cellular phosphoproteins. This compound is principally known to be useful for the treatment of positive and negative symptoms of schizophrenia, depression (especially acute depression and bipolar depression), anxiety and traumatic disorders (including acute anxiety and post-traumatic stress disorder), and dementias (including Alzheimer's disease and the symptoms associated therewith). At dopamine D2 receptors, this compound has dual properties and acts as both a post-synaptic antagonist and a pre-synaptic partial agonist of the D2 receptor. It also stimulates phosphorylation of glutamatergic NMDA NR2B, or GluN2B, receptors in a mesolimbic specific manner. It is believed that this regional selectivity in the brain areas thought to mediate the efficacy of antipsychotic drugs, together with the serotonergic, glutamatergic, and dopaminergic interactions, may result in antipsychotic efficacy for positive, negative, affective and cognitive symptoms associated with schizophrenia. The compound also exhibits serotonin reuptake inhibition, providing antidepressant activity for the treatment of schizoaffective disorder, co-morbid depression, and/or as a stand-alone treatment for major depressive disorder. Lumateperone is also useful for the treatment of bipolar disorder and other psychiatric and neurodegenerative disorders, particularly behavioral disturbances associated with dementia, autism and other CNS diseases. These features may be able to improve the quality of life of patients with schizophrenia and enhance social function to allow them to more fully integrate into their families and their workplace. Lumateperone displays differential dose-dependent effects, selectively targeting the 5-$HT_{2A}$ receptor at low doses, while progressively interacting with the D2 receptor at higher doses. As a result, at lower doses, it is useful in treating sleep, aggression and agitation. At a high dose, it can treat acute exacerbated and residual schizophrenia, bipolar disorders, and mood disorders.

Lumateperone, having the formula:

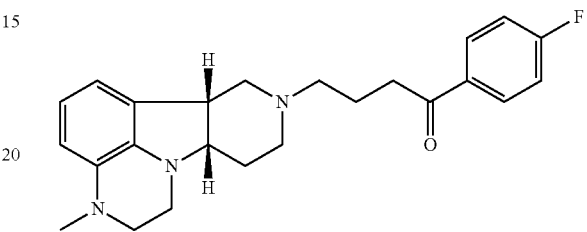

is a novel therapeutic agent with potent (Ki=0.5 nM) 5-$HT_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone is in Phase III clinical development as a treatment for schizophrenia, bipolar depression and agitation in dementia, including Alzheimer's Disease.

Lumateperone and related compounds have been disclosed in U.S. Pat. Nos. 6,548,493; 7,238,690; 6,552,017; 6,713,471; U.S. RE39680, and U.S. RE39679, as novel compounds useful for the treatment of disorders associated with 5-HT2A receptor modulation such as anxiety, depression, psychosis, schizophrenia, sleep disorders, sexual disorders, migraine, conditions associated with cephalic pain, and social phobias. U.S. Pat. Nos. 7,081,455 and 8,309,722 also disclose methods of making substituted heterocycle fused gamma-carbolines and uses of these gamma-carbolines as serotonin agonists and antagonists useful for the control and prevention of central nervous system disorders such as addictive behavior and sleep disorders. U.S. Pat. No. 8,598,119 and US 2015/0080404, each incorporated herein by reference, disclose the use of specific substituted heterocycle fused gamma-carbolines for the treatment of a combination of psychosis and depressive disorders as well as sleep, depressive and/or mood disorders in patients with psychosis or Parkinson's disease and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia. U.S. Pat. No. 8,648,077, incorporated herein by reference, discloses methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone.

U.S. Pat. No. 8,993,572, incorporated herein by reference, discloses prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy)butyl moiety are shown to have high selectivity for the serotonin transporter (SERT) relative to the heterocycle fused gamma-carboline containing 4-fluorophenylbutanone.

U.S. Pat. No. 8,598,119 teaches that selected substituted heterocycle fused gamma-carboline compounds have nanomolar affinity for the serotonin reuptake transporter (SERT) and so are selective serotonin reuptake inhibitors.

It has also recently been found that lumateperone may be particularly effective in treating acute depression and acute anxiety owing to its rapid onset of action compared to existing antidepressants. This is believed to be due to its signaling through a neurotransmitter system separate from the traditional monoamine signaling systems. Lumateperone provides a dopamine D1 receptor-dependent enhancement of NMDA and AMPA currents coupled with activation of the mTOR (e.g., mTORC1) signaling pathway.

BRIEF SUMMARY OF THE INVENTION

The present disclosure provides pharmaceutical capsules comprising lumateperone in free or pharmaceutically acceptable salt form. In some embodiments, the capsule is an oral capsule. In some embodiments the capsule further comprises one or more additional therapeutic agents. These capsules are useful for the treatment or prophylaxis of a variety of central nervous system disorders.

DETAILED DESCRIPTION

Lumateperone is a novel therapeutic agent with potent (Ki=0.5 nM) 5-HT$_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone is in Phase III clinical development as a treatment for schizophrenia, bipolar depression and agitation in dementia, including Alzheimer's Disease.

The present disclosure provides a pharmaceutical capsule (Capsule 1), comprising lumateperone:

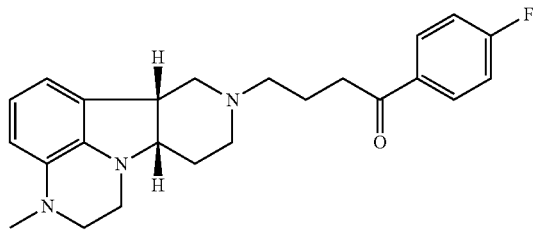 [SMILES: CN1CCN2c3c(cccc31)[C@@H]1CN(CCCC(=O)c3ccc(F)cc3)CC[C@@H]12]

in free or pharmaceutically acceptable salt form (e.g., in tosylate salt form). For example, Capsule 1 may be as follows:
1.1. Capsule 1, wherein the capsule comprises lumateperone in free base form (e.g., in free base solid amorphous dispersion form);
1.2. Capsule 1, wherein the capsule comprises lumateperone in pharmaceutically acceptable salt or co-crystal form;
1.3. Capsule 1, wherein the capsule comprises lumateperone in tosylate salt form, e.g., in one or more of mono-tosylate salt form, di-tosylate salt form, and tri-tosylate salt form;
1.4. Capsule 1.3, wherein the capsule comprises a combination of lumateperone in mono-tosylate salt form and lumateperone in di-tosylate salt form;
1.5. Any of Capsules 1 or 1.1-1.3, wherein the Capsule comprises lumateperone in mono-tosylate salt form;
1.6. Capsule 1.5, wherein the lumateperone mono-tosylate is in solid crystal form, e.g., having the physical and chemical properties as disclosed in U.S. Pat. No. 8,648,077, such as one or more of the XRPD spectrum, IR spectrum, and/or DSC/TGA spectrum as disclosed therein;
1.7. Capsule 1.5, wherein the lumateperone mono-tosylate is in solid crystal form, wherein the crystal exhibits an X-ray powder diffraction pattern comprising at least two peaks having 2-theta values selected from the group consisting of 5.68°, 12.11°, 16.04°, 17.03°, 18.16°, 19.00°, 21.67°, 22.55°, 23.48° and 24.30°, each of said peaks±0.2°, e.g., wherein the X-ray powder diffraction data is collected on a diffractometer operating with a copper anode with a nickel filter;
1.8. Capsule 1.5, wherein the lumateperone mono-tosylate is in solid crystal form, wherein the crystal exhibits an X-ray powder diffraction pattern comprising at least five peaks having 2-theta values selected from the group consisting of: 5.68°, 12.11°, 16.04°, 17.03°, 18.16°, 19.00°, 21.67°, 22.55°, 23.48° and 24.30°, each of said peaks±0.2°, e.g., wherein the X-ray powder diffraction data is collected on a diffractometer operating with a copper anode with a nickel filter;
1.9. Capsule 1.5, wherein the lumateperone mono-tosylate is in solid crystal form, wherein the crystal exhibits an X-ray powder diffraction pattern comprising the following peaks having 2-theta values: 5.6811°, 8.5140°, 11.3750°, 12.1088°, 13.3354°, 15.7948°, 16.0419°, 16.4461°, 17.0309°, 17.2606°, 17.5531°, 18.1581°, 18.9968°, 19.8889°, 20.7510°, 21.6724°, 22.25463°, 23.4815°, 23.7411°, 24.3006°, 25.9394°, 27.2321°, 28.3782°, 28.9055°, 29.6695°, 31.6106°, 32.2950°, 34.8530°, 37.5435°, 39.4972°, 40.2502° and 40.8303°, each of said peaks±0.2°, e.g., wherein the X-ray powder diffraction data is collected on a diffractometer operating with a copper anode with a nickel filter;
1.10. Any of Capsules 1.5-1.9, wherein the Capsule further comprises toluenesulfonic acid, e.g., in a molar ratio of about 1:1 to 1:2 with respect to the lumateperone monotosylate, e.g., 1:1 to 1:1.5 molar ratio, or 1:1 to 1:2 molar ratio, or about a 1:1 molar ratio;
1.11. Capsule 1 or any of 1.1-1.10, wherein the Capsule comprises the lumateperone, in free and/or pharmaceutically acceptable salt form in a total unit amount equivalent to 0.01 to 120 mg of lumateperone free base, e.g., 0.01 to 100 mg, 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, 30 mg to 50 mg, 50 to 100 mg, 1 to 75 mg, or 1 to 60 mg, or 1 to 40 mg, or 1 to 20 mg, 1 to 10 mg, 25 to 35 mg, or 35 to 45 mg, or about 6 mg, or about 14 mg, or about 28 mg, or about 42 mg; for example, the Capsule may comprise about 20 mg, about 40 mg, or about 60 mg of lumateperone in monotosylate salt form;
1.12. Capsule 1 or any of 1.1-1.11, further comprising one or more pharmaceutically acceptable diluents or carriers (i.e., excipients);
1.13. Capsule 1.12, wherein the one or more pharmaceutically acceptable diluents or carriers comprises one or more of (a) diluent/filler (e.g., cellulose or microcrystalline cellulose, mannitol, dicalcium phosphate, or isomalt), (b) binder, (c) disintegrant (e.g., crospovidone or croscarmellose sodium), (d) lubricant (e.g., magnesium stearate or glyceryl monostearate), (e) a glidant (e.g., silicon dioxide or talc), (f) effervescent, (g) polymer, (h) plasticizer, (i) drying agent or desiccant, (j) humectant (e.g., polyol), (k) wetting agent, (l) anti-oxidant, (m) thickening agent (e.g., gelling agent), (n) surfactant, (o) buffer, (p) sweetener or flavor, and (q) dye or colorant;

1.14. Capsule 1.12, wherein the one or more pharmaceutically acceptable diluents or carriers comprises one or more hydrophilic water-soluble or water swellable polymers;

1.15. Capsule 1.14, wherein the polymer is selected from the group consisting of natural or modified cellulosic polymers, polymers of ethylene oxide and/or propylene oxide, polymers comprising acrylic acid monomers, natural or modified gums (e.g. xanthan gum), natural or modified starches (e.g., pre-gelatinized starches), or any mixture thereof;

1.16. Capsule 1.12, wherein the one or more pharmaceutically acceptable diluents or carriers comprises one or more hydrophobic polymers or poorly water-soluble polymers, for example, a silicone polymer, or polyalkylene polymer (e.g., polyethylene);

1.17. Capsule 1.12, wherein the one or more pharmaceutically acceptable diluents or carriers comprises are selected from any of the following: alcohols (ethanol, glycerol, propylene glycol), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropyl methyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinyl pyrrolidones, polyethylene oxide and/or polypropylene oxide polymers and copolymers (e.g., poloxamers, such as poloxamer 188), polyacrylate polymers (e.g., carbopols), polyamide polymers, sugars and sugar alcohols (e.g., dextrose, lactose, galactose, glucose, ribose, sucrose, trehalose, mannitol, maltitol, lactitol, sorbitol, xylitol, erythritol, galactitol, inositol), polypeptides/proteins, amino acids, inorganic or organic acids (e.g., citric acid, lactic acid, malic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzene sulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine), nonionic surfactants (e.g., fatty alcohol ethoxylates (e.g., polyethylene glycol polydodecyl ethers)), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), and antioxidants (e.g., ascorbic acid, ascorbyl palmitate, sodium meta-bisulfite, sodium sulfite, BHT, BHA, TBHQ, propyl gallate, beta-carotene, tocopherols, tocotrienols, citric acid, EDTA);

1.18. Capsule 1 or any of 1.1-1.17, wherein the capsule comprises or consists of (a) lumateperone tosylate (e.g., mono-tosylate), mannitol, croscarmellose sodium, talc, and glyceryl monostearate, or (b) lumateperone tosylate (e.g., mono-tosylate), mannitol, croscarmellose sodium, talc, and magnesium stearate;

1.19. Any of Capsules 1.12-1.18, wherein any one or more of each said pharmaceutically acceptable carriers or diluents are present in an amount of 0.01 to 80% by weight of the Capsule, e.g., 0.1 to 60%, or 0.1 to 40%, or 0.1 to 30%, 0.01 to 15%, or 0.01 to 10%, or 0.1 to 20%, or 0.1 to 15% or 0.1 to 10%, or 0.5 to 10%, or 0.5 to 5%, or 1 to 5%, or 2.5 to 5%, or 1 to 3%, or 0.1 to 1%; optionally wherein the Capsule comprises from 60 to 90% by weight of diluent/filler, e.g., 70 to 80% diluent/filler;

1.20. Any of Capsules 1.12-1.19, wherein the Capsule comprises from 1% to 90% lumateperone, in free and/or in pharmaceutically acceptable salt form (e.g. tosylate), by weight of the composition and measured as the total content of lumateperone in all forms thereof, e.g., 1% to 80%, or 1% to 70%, or 1% to 60%, or 1% to 50%, or 1% to 40%, or 1% to 30%, or 1% to 20% or 1% to 15%, or 1% to 10%, or 1% to 5%, or 5% to 10%, or 10% to 20%, or 20 to 30%, lumateperone, in free and/or pharmaceutically acceptable salt form;

1.21. Any preceding Capsule, wherein the capsule comprises from 0.01 to 99% water, for example, from 0.01 to 10% water, or from 0.01 to 5% water, or from 50 to 99% water, or from 75 to 99% water, or from 25 to 75% water;

1.22. Any preceding Capsule, wherein the capsule comprises one or more surface coatings, e.g., polymer surface coatings;

1.23. Any preceding Capsule wherein the Capsule is a hard-shelled capsule, e.g., wherein said capsule contains lumateperone, in free or pharmaceutically acceptable salt form in admixture with one or more pharmaceutically acceptable diluents or carriers, optionally further in admixture with one or more other therapeutic agents, and said lumateperone and diluents/carriers and other agents are comprised as granules or pellets, or as a powder, said granules, pellets or powder being contained within the capsule shell;

1.24. Any preceding Capsule wherein the Capsule is a soft-shelled capsule, e.g., a gel capsule;

1.25. Any preceding Capsule wherein the lumateperone is present in (a) a mean particle size of 1 to 200 μm, e.g., 1 to 150 μm, 1 to 100 μm, 1 to 50 μm, 1 to 25 μm, 1 to 15 μm, 1 to 10 μm, 5 to 10 μm, or 1 to 5 μm; and/or (b) a D90 of 100 μm or less, 50 μm or less, 25 μm or less, 15 μm or less, or 10 μm or less; and/or (c) a D10 of 50 μm or less, 25 μm or less, 15 μm or less, or 10 μm or less, or 5 μm or less; optionally wherein the lumateperone particles have a D90 of not more than 10 μm, a D10 of not more than 5 μm, and/or a particle size distribution (PSD) D50 of 2 to 5 μm;

1.26. Capsule 1 or any of 1.1-1.25, wherein the Capsule is formulated for oral (gastrointestinal) administration;

1.27. Capsule 1 or any of 1.1-1.25, wherein the Capsule is formulated for rectal or vaginal administration;

1.28. Any foregoing Capsule wherein the lumateperone is in combination (e.g. a fixed combination) with an effective amount of an additional therapeutic agent;

1.29. Capsule 1.28, wherein the additional therapeutic agent is an anxiolytic or antidepressant agent;

1.30. Capsule 1.29, wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:
  (a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
  (b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
  (c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
  (d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

1.31. Capsule 1.29, wherein the additional antidepressant agent is selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

1.32. Capsule 1.28, wherein the additional therapeutic agent is a NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof;

1.33. Any preceding Capsule, wherein the Capsule is manufactured by adding a solid material comprising the lumateperone, in free or pharmaceutically acceptable salt form, to an empty capsule shell and sealing said shell closed;

1.34. Capsule 1.33, wherein said solid material is manufactured by a dry-blending or dry-granulating process;

1.35. Capsule 1.33 or 1.34, wherein said capsule shell comprises a gelling agent, e.g., gelatin, carrageenan, starch, cellulose, modified celluloses (e.g., HPMC, HPC, HEC, and the like), or a combination thereof;

1.36. Capsule 1.35, wherein the capsule shell further comprises one or more of a plasticizer, lubricant, preservative, disintegrant, dye or colorant, flavor, sweetener, or other pharmaceutically acceptable carrier, diluent, or excipient, as described herein (e.g., wherein one or more of the pharmaceutically acceptable carriers, diluents or excipients described hereinbefore are comprised in the capsule shell);

1.37. Any preceding Capsule, wherein the Capsule is intended to be administered once daily, or twice daily, or three times daily, or every other day, or every third day;

1.38. Any preceding Capsule, wherein the Capsule is packaged in a blister pack (e.g., push-through pack), e.g., a blister pack made of any suitable material (e.g., aluminum foil, polyvinyl chloride, polyvinylidene chloride, polychlorotrifluoroethylene, cyclic olefin copolymers, polyethylene, polypropylene, polyethylene terephthalate, or a combination thereof);

1.39. Any preceding capsule, wherein the Capsule is packaged in a bottle (e.g., plastic or glass, optionally with a screw cap lid or a child-proof lid), optionally wherein the bottle also contains a desiccant (e.g., silica or calcium chloride), for example, wherein the bottle has a compartment to hold a desiccant or wherein the bottle contains one or more small water-permeable bags containing the desiccant;

1.40. Any preceding capsule, wherein the capsule is formulated for immediate-release;

1.41. Any preceding capsule, wherein the capsule has the formula shown for any of Batch 1, Batch 2, Batch 3, Batch 4, Batch 5 or Batch 6 in Example 2 herein;

1.42. Any preceding capsule, wherein a single capsule dissolves in 500 mL of 0.1N aqueous hydrochloric acid to the extent of at least 85% after 15 minutes (e.g., 90-98%), and/or to the extent of at least 92% after 30 minutes (e.g., 95-99%), and/or at least 94% after 45 minutes (e.g., 95-99%);

1.43. Any preceding capsule, wherein administration of an oral dose of a single capsule comprising 60 mg of lumateperone tosylate under fasting conditions provides a maximal plasma concentration of lumateperone of 15-55 ng/mL (e.g., a mean Cmax of 30-40 ng/mL), and/or a time to maximal plasma concentration of lumateperone of 0.7 to 1.5 hours (e.g., a mean Tmax of 1-1.2 hours, or a median Tmax of about 1 hour), and/or an area under the plasma concentration curve (AUC) extrapolated to infinity (AUC(0-inf)) of 51 to 135 hours-ng/mL (e.g., a mean AUC(0-inf.) of 70 to 115 hr-ng/mL, or 85 to 100 hr-ng/mL);

1.44. Any preceding capsule, wherein administration of an oral dose of a single capsule comprising 60 mg of lumateperone tosylate under fasting conditions provides one or more of the following plasma metabolite values:
  (a) a mean Cmax for Metabolite A of 25-38 ng/mL (e.g., 32 ng/mL);
  (b) a mean Cmax for Metabolite B of 16-25 ng/mL (e.g., 20 ng/mL);
  (c) a mean Cmax for Metabolite C of 16-25 ng/mL (e.g., 20 ng/mL);
  (d) a mean Cmax for Metabolite D of 8-13 ng/mL (e.g., 10 ng/mL);
  (e) a mean Cmax for Metabolite E of 16-25 ng/mL (e.g., 20 ng/mL);
  (f) a mean AUC(o-inf) for Metabolite A of 270-410 hr-ng/mL (e.g., 340 hr-ng/mL);
  (g) a mean AUC(o-inf) for Metabolite B of 43-65 hr-ng/mL (e.g., 54 hr-ng/mL);
  (h) a mean AUC(o-inf) for Metabolite C of 220-335 hr-ng/mL (e.g., 278 hr-ng/mL);
  (i) a mean AUC(o-inf) for Metabolite D of 45-68 hr-ng/mL (e.g., 57 hr-ng/mL);
  (j) a mean AUC(o-inf) for Metabolite E of 330-500 hr-ng/mL (e.g., 415 hr-ng/mL);
  (k) a ratio of Cmax (metabolite A)/Cmax (lumateperone) of 0.8-1.3 (e.g., 1.1);
  (l) a ratio of Cmax (metabolite B)/Cmax (lumateperone) of 0.5-0.8 (e.g., 0.7);

(m) a ratio of Cmax (metabolite C)/Cmax (lumateperone) of 0.5-0.8 (e.g., 0.7);

(n) a ratio of Cmax (metabolite D)/Cmax (lumateperone) of 0.3-0.4 (e.g., 0.35);

(o) a ratio of Cmax (metabolite E)/Cmax (lumateperone) of 0.5-0.8 (e.g., 0.7);

(p) a ratio of AUC(o-inf)(metabolite A)/AUC(0-inf)(lumateperone) of 3.2-4.8 (e.g. 4.0);

(q) a ratio of AUC(o-inf)(metabolite B)/AUC(0-inf)(lumateperone) of 0.5-0.8 (e.g. 0.6);

(r) a ratio of AUC(o-inf)(metabolite C)/AUC(0-inf)(lumateperone) of 2.6-4.0 (e.g. 3.3);

(s) a ratio of AUC(o-inf)(metabolite D)/AUC(0-inf)(lumateperone) of 0.5-0.8 (e.g. 0.7);

(t) a ratio of AUC(o-inf)(metabolite E)/AUC(0-inf)(lumateperone) of 3.9-6.0 (e.g. 5.0);

1.45. Any preceding capsule, wherein the capsule is formulated for delayed or sustained release.

In some embodiments, binders may include one or more of hydroxypropyl cellulose, hydroxypropyl methylcellulose, ethyl cellulose, methylcellulose, polyvinyl pyrrolidone, povidone, polyvinyl alcohol, gum arabic powder, gelatin, pullulan and the like. Each capsule may comprise from 0.5-10% by weight, e.g., 1-5%, or 1-3% by weight each binder.

Carmellose calcium, croscarmellose sodium, sodium starch glycolate, crospovidone, low substituted hydroxypropyl cellulose, powdered agar and the like are used as the disintegrant. The disintegrants such as sodium starch glycolate, croscarmellose sodium and low substituted hydroxypropyl cellulose are preferable. Each tablet can contain 0.1-15% by weight, preferably 1-5% by weight of the disintegrant.

In some embodiments, the capsule of the present disclosure further comprises an appropriate amount of a flavor, a lubricant, a coloring agent and the like, or various additives which are commonly used for preparing a galenic formulation. Optionally, any of such additives may be comprised in the capsule shell, or within the capsule or both. If comprised within the capsule, such additives may be incorporated within the granules, pellets or powder material which comprises the lumateperone, or such additives may be comprised in granules, pellets or powder material separate from the granules, pellets or powder comprising the lumateperone. Lubricants may include magnesium stearate, calcium stearate, sucrose fatty acid ester, polyethylene glycol, talc, stearic acid, sodium stearyl fumarate and the like. Coloring agents may include the food colors such as food yellow no. 5, food red no. 2, food blue no. 2, food lake colors, iron sesquioxide and the like.

In some embodiments, a coating mixture may be applied to the capsule by using a well-known method with the purpose of, for example, further masking of a taste and an odor, and preparation of an enteric formulation or a sustained-release formulation after coating a particle core with the active ingredient, one or more additives and the like.

The capsules of the present disclosure include, for example, hard-shelled capsules and soft-shelled capsules. They do not include tablets, caplets, and pills. Hard capsules are two-piece gel encapsulations of solid material. The capsule shell consists of two halves, an outer half and an inner half, which when joined and sealed form a secure enclosure for the solid material contained therein. The active pharmaceutical ingredient, i.e., the lumateperone, may be comprised as a powder, or as one or more granules or pellets within the capsule. Such granules or pellets may be manufactured by any suitable means, including extrusion and spheronization of a powder, roller compaction, or slugging. Soft-shelled capsules are single-piece gel encapsulations of solid material, and such solid material may be in the form of an aqueous gel.

The capsules of the present disclosure may further include any one or more of pharmaceutically acceptable solvents, surface tension modifiers (e.g., surfactants), preservatives, antioxidants, colorants, taste masking agents, flavors and sweeteners. Examples of solvents include water and other solvents, which are miscible with water or solubilizing agents and suitable for oral purposes. Examples of suitable solvents are ethanol, propylene glycol, glycerol, polyethylene glycols, poloxamers, sorbitol and benzyl alcohol. In some embodiments, the aqueous solubility of the lumateperone may further be enhanced by the addition to the solution of a pharmaceutically acceptable co-solvent, a cyclodextrin or a derivative thereof (e.g. dextrans).

Preservative agents may be added to prevent the growth of microorganisms such as bacteria, yeasts and fungi in liquid formulations, which are likely to be used repeatedly. Suitable preservatives should be physicochemical stable and effective in the desired pH range. Examples of preservative agents include ethanol, methylparaben, propylparaben and benzyl alcohol.

In some embodiments, the capsules of the present disclosure include one or more antioxidants to guard against degradation of the active. Examples of antioxidants include propyl gallate, ascorbyl palmitate, ascorbic acid, t-butylhydroquinone (TBHQ), butylated hydroxyanisole (BHA), butylated hydroxytoluene (BHT), tocopherols, tocotrienols, sodium sulfite, sodium metabisulfite, beta-carotene, citric acid and EDTA.

In some embodiments, coloring agents may be used to introduce a uniformity of appearance to the product and/or to protect any light-sensitive ingredients. Suitable coloring agents include all pigments, dyes and lakes approved by the U.S. Food and Drug Administration (e.g., FD&C colorants), including but not limited to FD&C Yellow #6, FD&C Blue #1, FD&C Red #3, black iron oxide, red iron oxide, titanium dioxide, or any combination thereof. Coloring agents may be included within the capsule shell or within the capsule fill, or both.

In some embodiments, sweetening agents may be used to mask unpleasant taste or to achieve a desired taste. Examples of sweetening agents are glucose, sorbitol, glycerol, acesulfame potassium and neohesperidin dihydrochalcon. The taste may be optimized further by the addition of one or more flavoring substances. Suitable flavoring substances are fruit flavors such as cherry, raspberry, black currant, lemon or strawberry flavor or other flavors such as liquorice, anise, peppermint, and caramel.

The capsules of the present disclosure may be prepared by, for example, wet granulating lumateperone, in free or pharmaceutically acceptable salt form, and one or more pharmaceutically acceptable carriers or diluents (i.e., excipients), for example, a binder and/or a disintegrant with water or a binder solution, using a machine such as a high speed mixer granulator, a fluidized-bed granulator dryer, a centrifugal tumbling fluidized-bed granulator coating machine or a kneading machine; blending or spraying a lubricant to the granules; and then subjecting to encapsulation. Alternatively, the capsules of the present disclosure can be prepared by dry granulating lumateperone, in free or pharmaceutically acceptable salt form, and one or more pharmaceutically acceptable carriers or diluents (i.e., excipients), for example, a binder (a disintegrant may be further contained), using a machine such as a roller compactor; blending or spraying a disintegrant (a lubricant may be further contained) to the granules; and then subjecting to encapsulation.

Suitable forms of lumateperone include the free base form, including amorphous solid dispersions thereof, pharmaceutically acceptable salt forms, including crystal forms thereof, and pharmaceutically acceptable co-crystal forms. Amorphous solid dispersion forms of lumateperone free base are disclosed in patent publication WO 2018/71233, the contents of which are hereby incorporated by reference in its entirety. Unless otherwise indicated, the term "pharmaceutically acceptable salt" includes acid addition salts between lumateperone and any pharmaceutically acceptable acid (e.g., Bronsted acid) in any molar ratio permitted by the structure of the acid. For example, "pharmaceutically acceptable salt form" of lumateperone includes the monohydrochloride, the di-hydrochloride, the tri-hydrochloride, the mono-tosylate, the di-tosylate and the tri-tosylate, or any mixtures thereof. In some embodiments, the lumateperone salt is a crystalline solid (e.g., a salt crystal). In some embodiments, the lumateperone may exist as a co-crystal, i.e., lumateperone free base co-crystallized with a second species. Pharmaceutically acceptable salt and co-crystal forms of lumateperone include all those forms disclosed in U.S. Pat. Nos. 8,648,077, 9,199,995, and 9,586,960, and patent publications WO 2017/1172811 and WO 2017/172784, and U.S. provisional applications 62/563,341 and 62/681,534, the contents of each of which are hereby incorporated by reference in their entireties.

In a second aspect, the present disclosure provides a process (Process 1) for the manufacture of Capsule 1, or any of 1.1-1.45, wherein the process comprises the steps of:
(a) combining lumateperone, in free or pharmaceutically acceptable salt form (e.g., tosylate salt form), with at least one diluent or carrier (e.g., with a filler, such as mannitol);
(b) blending the resulting the mixture;
(c) optionally filtering (e.g., screening) the resulting mixture, e.g., to achieve a uniform particle size;
(d) adding at least one other diluent or carrier (e.g., a disintegrant (e.g., croscarmellose sodium), or a glidant (e.g., talc), or a lubricant (e.g., magnesium stearate), or a combination thereof);
(e) blending the resulting mixture;
(f) optionally filtering (e.g. screening) the resulting mixture, e.g., to achieve a uniform particle size;
(g) encapsulating the resulting material, e.g., into hard-walled capsules;
(h) optionally applying one or more coatings to the capsule.

In a third aspect, the present disclosure provides a method (Method 1) for the treatment or prophylaxis of a disease or disorder involving or mediated by the 5-HT$_{2A}$ receptor, serotonin transporter (SERT), and/or dopamine D1/D2 receptor signaling pathways, comprising administering to a patient in need thereof the capsule according to Capsule 1 or any of 1.1-1.45. In some embodiments, said disease or disorder is selected from obesity, anorexia, bulimia, depression (including major depressive disorder (MDD), acute depression, post-traumatic depression), anxiety (including acute anxiety, panic disorders, phobias, social anxiety disorder, or social withdrawal), psychosis (including acute psychosis), schizophrenia (including residual symptoms of schizophrenia, such as positive and/or negative symptoms of schizophrenia), obsessive-compulsive disorder, sexual disorders, migraine, attention deficit disorder, attention deficit hyperactivity disorder, sleep disorders, conditions associated with cephalic pain, anger disorders, agitation (including acute agitation), dementia (including Alzheimer's Disease and Parkinson's dementia), gastrointestinal disorders such as dysfunction of gastrointestinal tract motility, and bipolar disorder (e.g., bipolar depression).

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

Methods of synthesizing lumateperone and related compounds are known in art, and include the methods disclosed in in U.S. Pat. Nos. 6,548,493; 7,238,690; 6,552,017; 6,713,471; 7,183,282; 7,081,455; 8,309,722; U.S. RE39680, and U.S. RE39679, and US 2017/183350, the contents of each of which are incorporated by reference in their entirety. Salts of the Compounds of the Invention may also be prepared as similarly described in U.S. Pat. Nos. 6,548,493; 7,238,690; 6,552,017; 6,713,471; 7,183,282; 8,648,077; U.S. RE39680; U.S. RE39679; the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

The pharmaceutically acceptable salts of lumateperone can be synthesized from the parent compound, which contains basic moieties, by reaction with a suitable acid, by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred.

Dosages employed in practicing the present disclosure will of course vary depending, e.g. on the particular disease or condition to be treated, the particular active compounds used, the mode of administration, and the therapy desired. Unless otherwise indicated, an amount of an active compound for administration (whether administered as a free base or as a salt form) refers to or is based on the amount of the compound in free form (i.e., the calculation of the amount is based on the amount of active moiety in free form, not taking into account the weight of the counter ion in the case of a salt).

For the avoidance of doubt, any disclosure of a numerical range, e.g., "up to X" amount is intended to include the upper numerical limit X. Therefore, a disclosure of "up to 60 mg" is intended to include 60 mg.

EXAMPLE 1: EXCIPIENT COMPATIBILITY STUDY

The chemical compatibility of lumateperone monotosylate with selected excipients is studied. Excipients evaluated are (1) Fillers (microcrystalline cellulose, mannitol, anhydrous dicalcium phosphate, and isomalt); (2) Disintegrants (crospovidone, and croscarmellose sodium); (3) Glidants (colloidal silicon dioxide, and talc); and (4) Lubricants (magnesium stearate, and glyceryl monostearate); and (5) Gelatin. Lumateperone tosylate is mixed in a 1:1 weight ratio with each excipient and the mixture is evaluated immediately after mixing, as well as after 4 weeks of accelerated aging at 40° C. and 75% relative humidity, and at 4 weeks at 50° C. Comparisons are made to lumateperone tosylate under the same conditions without excipient. It is found that there are no chemical incompatibilities with the selected excipients. All samples measurements indicate lumateperone tosylate potency of 95.2% to 106.5% compared to control.

EXAMPLE 2: SMALL SCALE TESTING OF CAPSULE FORMULATIONS

Initial trials of capsule formulation development are performed for capsules comprising 42 mg lumateperone (as 60 mg lumateperone monotosylate). Each formulation comprises a single filler, a single disintegrant, a single glidant, and a single lubricant selected from the excipients studied in Example 1. Formulations are prepared in 300 g batch sizes. The initial dry-blend process includes screening both the API (lumateperone tosylate) and each excipient through a 30-mesh screen, followed by manual bag blending. The API and all excipients, other than lubricant, are blended first, followed by addition of lubricant, and further blending. The resulting mixture is then encapsulated into Size 0 gelatin capsules using a bench top filling machine using dosing discs and tamping pins to obtain consistent fill weights. The Table below shows the compositions tested (ingredients are shown in weight percent of 300 mg capsule net fill weight):

|  | Batch | | | | |
| --- | --- | --- | --- | --- | --- |
|  | 1 | 2* | 3 | 4 | 5* |
| Lumateperone tosylate | 20.0% | 20.0% | 20.0% | 20.0% | 20.0% |
| Microcrystalline cellulose | 73.7% | | | | |
| Mannitol | | 73.7% | | | 73.7% |
| Dicalcium phosphate, Anhydrous | | | 73.7% | | |
| Isomalt | | | | 73.7% | |
| Crospovidone | 5.0% | | 5.0% | | |
| Croscarmellose sodium | | 5.0% | | 5.0% | 5.0% |
| Colloidal silicon dioxide | 0.30% | | 0.30% | | |
| Talc | | 0.30% | | 0.30% | 0.30% |
| Magnesium stearate | 1.0% | | 1.0% | | |
| Glyceryl monostearate | | 1.0% | | 1.0% | 1.0% |

*Batches 1-4 are initial test batches; Batch 5 has the same composition as Batch 2 and was prepared for further studies It is found that Batch 2 had no formulation process issues, whereas Batches 1, 3, and 4 required running the encapsulator at lower speed to avoid the blend sticking to the tamping pins. This sticking results in inconsistent fill weights and a high number of rejected capsules.

Each batch is tested in a standard dissolution study using 500 mL of 0.1N aqueous hydrochloric acid as the dissolution media. The results are shown in the table below. Results are similar across Batches 1, 2, and 3, but Batch 4 shows low assay and dissolution values. The result for Batch 2 is acceptable for an immediate release oral capsule, and this batch formula is therefore chosen for preparation of a second batch (Batch 5).

|  | Batch | | | | |
| --- | --- | --- | --- | --- | --- |
|  | 1 | 2* | 3 | 4 | 5* |
| Dissolution (%) at 15 min | 91 | 95 | 73 | 88 | 97 |
| Dissolution (%) at 30 min | 92 | 97 | 87 | 91 | 98 |
| Dissolution (%) at 45 min | 94 | 98 | 95 | 92 | 98 |
| Dissolution (%) at 60 min | 94 | 99 | — | — | 98 |
| Dissolution (%) at infinity (calc.) | 96 | 100 | 101 | 92 | — |
| Assay (%) | 100.7 | 97.1 | 98.7 | 94.8 | 98.8 |

A second 300 g batch according to the formula of Batch 2 is prepared for 3-month stability testing (Batch 5), except that this batch is prepared using a 1-quart mechanical V-Blender (which is a standard, scalable blending machine) instead of manual bag blending. The API and all excipients, other than the glyceryl monostearate (lubricant) are combined and blended at 25 rpm for 15 minutes. The glyceryl monostearate is then added and the mixture is blended at 25 rom for 3 minutes. Upon filling into the gelatin capsules, it is observed that there is some sticking of the blend to the tamping pins. The acceptance rate for filled capsules is 88%. The acceptable capsules are then packaged into 60 cc high density polyethylene (HDPE) bottles, 30 capsules to each bottle with no coil or desiccant in the bottles. The bottles are stored for 3 months at 40° C. and 75% relative humidity. Assay, dissolution rate and appearance are examined at 1 month and 3 months, and the results are shown in the table below. The capsules are all found to have no change in appearance and acceptable stability.

| Time | Initial | 1-Mo | 3-Mo |
| --- | --- | --- | --- |
| Dissolution (%) at 15 min | 97 | 96 | 100 |
| Dissolution (%) at 30 min | 98 | 97 | 101 |
| Dissolution (%) at 45 min | 98 | 97 | 101 |
| Dissolution (%) at 60 min | 98 | 97 | 101 |
| Assay (%) | 98.8 | 100.3 | 99.7 |
| Moisture (%) | 0.15 | 0.35 | 0.53 |

EXAMPLE 3: SCALE UP OF CAPSULE FORMULATION (GMP)

Further studies are performed to prepare 5.3 kg batches of lumateperone tosylate capsules for GMP evaluation (current Good Manufacturing Practices, as set by the U.S. Food & Drug Administration). Based on the small-scale study results, the Batch 2 formula is selected for further development, but with the lubricant changed to magnesium stearate and the preparation process modified to reduce sticking of the blend (the composition otherwise matches Batch 2 from Example 2). To improve the process, dry blending is used with a pre-blend step and manual screening of the pre-blend. Thus, the batch composition is as follows:

|  | Batch 6 |
| --- | --- |
| Lumateperone tosylate | 20.0% |
| Mannitol | 73.7% |
| Croscarmellose sodium | 5.0% |
| Talc | 0.30% |
| Magnesium stearate | 1.0% |
| Glyceryl monostearate | — |

Capsules comprising 60 mg lumateperone tosylate (42 mg lumateperone free base) are prepared. The API is first blended in a 16-quart V-Blender with approximately half of the total mannitol quantity. One-quarter of the total mannitol quantity is first added to the empty blender, followed by the API, followed by the remaining one-quarter of mannitol. The mixture is blended at 25 rpm for 10 minutes. This pre-blend is then discharged and screened through a 30-mesh screen. The screened pre-blend is then combined with all remaining excipients (including the remaining 50% of the mannitol), other than lubricant, in a 1 cubic foot V-Blender and blended for 20 minutes at 25 rpm. The lubricant, magnesium stearate, is then added and the mixture is blended for 3 minutes at 25 rpm. The blend is then encapsulated into Size 0 gelatin capsules. GMP analytical studies are performed, and it is found that the batch meets all GMP requirements. No adverse sticking of the blend to the tamping pins is observed.

The GMP study is repeated to prepare a batch of 20 mg lumateperone tosylate capsules (14 mg lumateperone free base). The composition is modified from that shown in Batch 2 of Example 2 as follows: the batch comprises 6.7% by weight of lumateperone tosylate, 1.25% by weight of magnesium stearate, and 86.8% by weight of mannitol. The lower quantity of lumateperone tosylate reflects the lower dose of the capsules. The lubricant level is increased to improve blending for the smaller dose, and the mannitol quantity is adjusted to q.s. In addition, due to the lower API content, the blending process is modified so that the pre-blend mixing is conducted for 15 minutes instead of 10 minutes to ensure proper blend uniformity. GMP analytical studies are performed, and it is found that the batch meets all GMP requirements. No adverse sticking of the blend to the tamping pins is observed.

Finally, both 14 and 42 mg lumateperone capsules are prepared on a 7.5 kg batch scale (25,000 capsules per batch, 300 mg fill weight per capsule), using the aforementioned process and compositions. GMP analytical studies are performed, and it is found that the batch meets all GMP requirements. No adverse sticking of the blend to the tamping pins is observed.

In further scale-ups, the manual screening step is replaced with mechanical screening through a Comil model 196S conical mill (0.045" diameter holes).

EXAMPLE 4: PHARMACOKINETICS

Batch 2 Formula

A phase I human clinical trial is conducted using the Batch 2 capsule formulation to determine plasma pharmacokinetic parameters for oral administration of a single 60-mg dose of lumateperone tosylate in schizophrenic volunteers. Six study subjects are enrolled in a three-part cross-over design with a 3-day washout period between doses to compare oral solution dosing (group A) to capsule dosing (group B) under fasting conditions, and to compare capsule dosing between fasting (group B) and fed conditions (group C). Subjects are randomly assigned to each dosing group dose with capsule first or oral solution first, followed by cross-over.

The oral solution is formed by reconstituting a single 60-mg capsule into 240 mL of Sprite Zero soft drink. Following ingestion of this oral solution, the study subject further consumes two 30 mL Sprite Zero rinses of the storage bottle to ensure that the entirety of the solution has been ingested. Subjects taking the single 60-mg capsule do so with 240 mL water. All subjects in groups A and B are fasted>10 hours prior to dosing. Subjects in group C are dosed shortly after a high-fat breakfast.

Blood samples for pharmacokinetic analysis were taken immediately prior to dosing (0 hours) and at 0.5 hours, 1 hour, 2, 3, 4, 6, 8, 12 and 24-hours post dose. Pharmacokinetic results are summarized in the table below (all measures are n=6):

| Parameter | Statistic | Group A Solution, fasted | Group B Capsule, fasted | Group C Capsule, fed |
|---|---|---|---|---|
| Cmax (ng/mL) | Mean | 33.4 | 25.4 | 15.4 |
|  | Median | 30.0 | 24.0 | 15.0 |
|  | Geo Mean | 29.3 | 22.6 | 8.5 |
| Tmax (h) | Median | 1.0 | 1.0 | 3.5 |
| AUC(0-t) | Mean | 80.5 | 76.9 | 77.5 |
| (h*ng/mL) | Median | 61.7 | 58.7 | 95.0 |
|  | Geo Mean | 69.3 | 60.1 | 40.4 |
| AUC(o-inf) | Mean | 81.2 | 77.9 | 79.0 |
| (h*ng/mL) | Median | 62.1 | 59.4 | 96.5 |
|  | Geo Mean | 69.9 | 60.9 | 43.0 |

Cmax is maximum plasma concentration. Tmax is time to Cmax. AUC(0-t) is the area under the plasma concentration curve from time zero to the last quantifiable time point. AUC(0-inf) is the area under the plasma concentration curve from time zero to infinity, as determined by extrapolating from the last quantifiable timepoint. The results show that the capsule formulation of Batch 2 provides generally comparable pharmacokinetics to the oral solution under fasting conditions. In contrast, dosing of the capsule under high-fat fed conditions results in a 38% lower median Cmax and a 60% higher median AUC values compared to fasting conditions. Note that because one subject was an outlier, showing extremely low plasma concentrations following fed dosing in Group C, median value are more informative for comparison than mean values.

Batch 6 Formula

A similar cross-over human clinical pharmacokinetic study is carried out using single-dose oral 60-mg lumateperone tosylate capsules according to the formula of Batch 6. Twenty-three study subjects are enrolled in a three-part cross-over design with a 7-day washout period between doses to compare fasted 60-mg capsule dosing (group A) to fasted 60-mg tablet dosing (group B), and to compare 60-mg capsule dosing between fasting (group B) and fed conditions (group C). Subjects are randomized as to the order of treatments received. All subject taking a single 60-mg capsule or tablet with 240 mL water in the morning. All subjects in groups A and B are fasted>10 hours prior to dosing. Subjects in group C are dosed shortly after an FDA-standard high-fat/high-calorie breakfast.

Blood samples for pharmacokinetic analysis were taken immediately prior to dosing (0 hours) and at 0.25 hours, 0.5 hours, 1 hour, 1.5, 2, 3, 4, 6, 8, 12 and 24-hours post dose. Pharmacokinetic results are summarized in the table below (all measures are n=21 for group A and n=23 for groups B and C):

| Parameter | Statistic | Group A Capsule, fasted | Group B Tablet, fasted | Group C Capsule, fed |
|---|---|---|---|---|
| Cmax (ng/mL) | Mean | 35.3 | 34.4 | 22.8 |
|  | Geo Mean | 30.3 | 28.2 | 20.1 |
| Tmax (h) | Median | 1.00 | 1.00 | 2.00 |
| AUC(0-t) | Mean | 89.6 | 90.6 | 97.3 |
| (h*ng/mL) | Geo Mean | 80.3 | 77.5 | 85.0 |
| AUC(0-inf) | Mean | 93.1 | 94.0 | 104.7 |
| (h*ng/mL) | Geo Mean | 83.8 | 80.9 | 91.5 |

The results show that the capsule formulation of Batch 6 provides generally comparable pharmacokinetics to the tablet under fasting conditions. In contrast, dosing of the capsule under high-fat fed conditions results in a 34% lower geometric mean Cmax and a 9% higher geometric mean AUC values compared to fasting conditions. Compared to the result seen for fasting and fed administration of 60-mg capsules according to Batch 2, the Batch 6 capsules generally result in higher AUC, higher Cmax, and a reduced food effect (AUC values only slightly increased for Batch 6 capsules taken with food, and Tmax significantly reduced compared to Batch 2 capsules taken with food).

Metabolite Pharmacokinetics

Lumateperone is metabolized both in the liver (hepatic first pass metabolism) in the intestines (presystemic metabolism). Metabolic pathways include direct glucuronidation, ketone reduction followed by O-glucuronidation, dealkylation of the N-methyl group, piperazine ring oxidation (lactam formation) and desaturation. Major circulating metabolites include the following compounds:

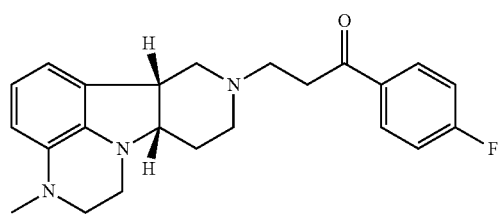
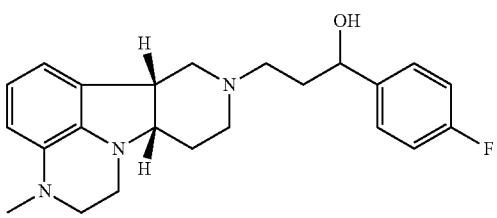

Metabolite A

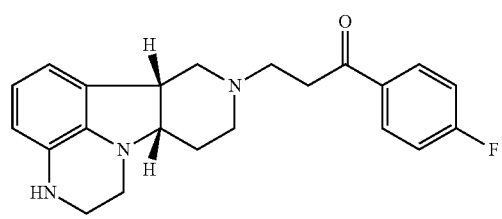
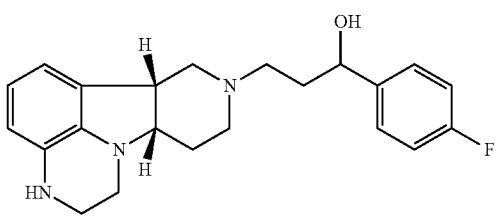

Metabolite B

Metabolite C

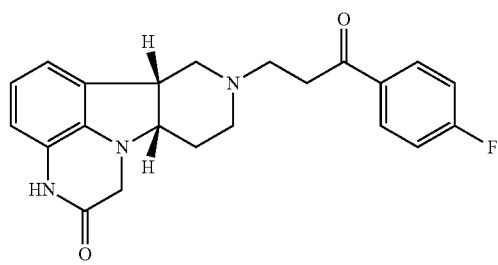
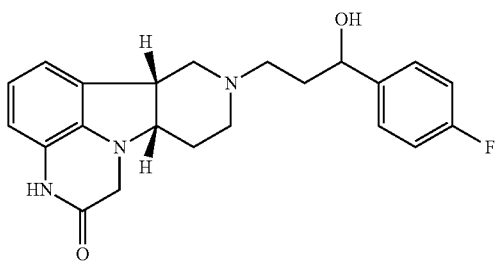

Metabolite E

Metabolite F

The Group A study subjects in the previously described cross-over pharmacokinetic study using the Batch 6 capsule formulation are also tested for these major metabolites in plasma from the same samples as described above. Cmax and AUC are calculated as provided above, and in addition, for each metabolite a ratio is generated between the parameter value for the metabolite compared to the same parameter value for the parent compound (as shown for Group A in the previous table). The following results are obtained:

| Parameter | Statistic | Group A (capsule, fasted) (n = 21) | | | | |
| --- | --- | --- | --- | --- | --- | --- |
| | | Metab A | Metab B | Metab C | Metab E | Metab F |
| Cmax | Geo Mean | 32.3 | 20.1 | 20.4 | 10.6 | 20.6 |
| (ng/mL) | Ratio* | 1.07 | 0.66 | 0.67 | 0.35 | 0.68 |
| AUC(0-t) | Geo Mean | 309.6 | 51.6 | 241.9 | 49.8 | 387.5 |
| (h*ng/mL) | Ratio* | 3.86 | 0.64 | 3.01 | 0.62 | 4.83 |
| AUC(0-inf) | Geo Mean | 339.7 | 53.9 | 278.3 | 56.8 | 415.0 |
| (h*ng/mL) | Ratio* | 4.05 | 0.64 | 3.32 | 0.68 | 4.95 |

We claim:
1. A pharmaceutical capsule for oral administration, comprising lumateperone:

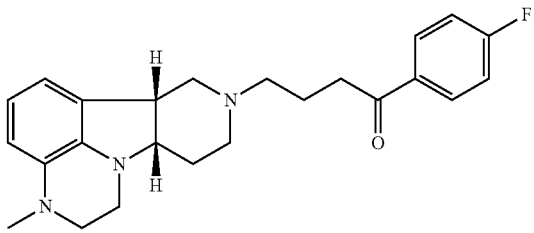 [SMILES: CN1CCN2c3c(cccc31)[C@@H]1CN(CCCC(=O)c3ccc(F)cc3)CC[C@@H]12]

in mono-tosylate salt form, wherein the lumateperone mono-tosylate is in solid crystal form;
wherein the capsule comprises the lumateperone mono-tosylate in an amount of about 60 mg lumateperone mono-tosylate in solid crystal form, and wherein the capsule comprises a blend of 10 to 30% by weight of lumateperone mono-tosylate in solid crystal form, and one or more pharmaceutically acceptable diluents or carriers comprising one or more of (a) diluent/filler, (b) binder, (c) disintegrant, (d) lubricant, or (e) a glidant, and wherein administration of an oral dose of a single capsule under fasting conditions provides a maximal plasma concentration of lumateperone of 15-55 ng/mL, and/or a time to maximal plasma concentration of lumateperone of 0.7 to 1.5 hours, and/or an area under the plasma concentration curve (AUC) extrapolated to infinity (AUC(0-inf)) of 51 to 135 hours-ng/mL.

2. The capsule of claim 1, wherein the capsule further comprises one or more colorants selected from FD&C Yellow #6, FD&C Blue #1, FD&C Red #3, black iron oxide, red iron oxide, titanium dioxide, or any combination thereof.

3. The capsule of claim 1, wherein the capsule comprises a blend of the 10 to 30% by weight of lumateperone mono-tosylate in solid crystal form, 60 to 90% by weight of mannitol, 0.5 to 10% by weight of croscarmellose sodium, 0.1 to 1% by weight of talc, and 0.1 to 3% by weight of magnesium stearate, filled into a gelatin capsule.

4. The capsule of claim 1, wherein the lumateperone mono-tosylate is in solid crystal form, and the crystal exhibits an X-ray powder diffraction pattern comprising at least two peaks having 2-theta values selected from the group consisting of 5.68°, 12.11°, 16.04°, 17.03°, 18.16°, 19.00°, 21.67°, 22.55°, 23.48° and 24.30°, each of said peaks±0.2°, wherein the X-ray powder diffraction data is collected on a diffractometer operating with a copper anode with a nickel filter.

5. The capsule of claim 3, wherein the capsule comprises a blend of the 10 to 30% by weight of lumateperone mono-tosylate in solid crystal form, 70 to 80% by weight of mannitol, 0.5 to 5% by weight of croscarmellose sodium, 0.1 to 1% by weight of talc, and 0.1 to 1% by weight of magnesium stearate, filled into the gelatin capsule.

6. The capsule of claim 1, wherein the capsule consists of a blend of the 10 to 30% by weight of lumateperone mono-tosylate in solid crystal form, about 74% by weight of mannitol, about 5% by weight of croscarmellose sodium, about 0.3% by weight of talc, and about 1% by weight magnesium stearate, filled into a gelatin capsule, wherein the gelatin capsule further comprises one or more colorants selected from FD&C Yellow #6, FD&C Blue #1, FD&C Red #3, black iron oxide, red iron oxide, titanium dioxide, or any combination thereof.

7. The capsule of claim 1, wherein the capsule consists of a blend of the 10 to 30% by weight of lumateperone mono-tosylate in solid crystal form, about 87% by weight of mannitol, about 5% by weight of croscarmellose sodium, about 0.3% by weight of talc, and about 1.25% by weight of magnesium stearate, filled into a gelatin capsule, wherein the gelatin capsule further comprises one or more colorants selected from FD&C Yellow #6, FD&C Blue #1, FD&C Red #3, black iron oxide, red iron oxide, titanium dioxide, or any combination thereof.

8. The capsule of claim 1, wherein the capsule comprises or consists of a blend of the 10 to 30% by weight of lumateperone mono-tosylate in solid crystal form and (a) mannitol, croscarmellose sodium, talc, and glyceryl monostearate, and gelatin, or (b) mannitol, croscarmellose sodium, talc, magnesium stearate, and gelatin.

9. The capsule of claim 1, wherein the capsule comprises one or more surface coatings.

10. The capsule of claim 1, wherein the capsule is a hard-shelled capsule.

11. The capsule of claim 1, wherein the lumateperone mono-tosylate in solid crystal form is present in (a) a mean particle size of 1 to 200 μm; and/or (b) a D90 of 100 μm or less; and/or (c) a D10 of 50 μm or less.

12. A method for treatment of a disease or disorder involving or mediated by a 5-HT$_{2A}$ receptor, serotonin transporter (SERT), and/or dopamine D1/D2 receptor signaling pathways, comprising administering to a patient in need thereof the capsule according to claim 1.

13. The capsule of claim 11, wherein the lumateperone mono-tosylate in solid crystal form is present in (a) a mean particle size of 1 to 5 μm; and/or (b) a D90 of 10 μm or less; and/or (c) a D10 of 5 μm or less.

14. The capsule of claim 13, wherein the lumateperone mono-tosylate in solid crystal form is present as particles having a D90 of not more than 10 μm, a D10 of not more than 5 μm, and/or a particle size distribution (PSD) D50 of 2 to 5 μm.

15. The capsule of claim 1, wherein the capsule dissolves in 500 ml of 0.1N aqueous hydrochloric acid to the extent of at least 85% after 15 minutes, and/or to the extent of at least 92% after 30 minutes, and/or at least 94% after 45 minutes.

16. The capsule of claim 1, wherein administration of an oral dose of a single capsule under fasting conditions provides a mean maximal plasma concentration (Cmax) of lumateperone of 30-40 ng/mL, and/or a mean time to maximal plasma concentration (Tmax) of lumateperone of 1-1.2 hours, and/or an area under the plasma concentration curve (AUC) extrapolated to infinity (AUC(0-inf)) of 70 to 115 hr-ng/mL.

17. The capsule of claim 16, wherein administration of an oral dose of a single capsule under fasting conditions provides a mean maximal plasma concentration (Cmax) of lumateperone of 30-40 ng/mL, and/or a mean time to maximal plasma concentration (Tmax) of lumateperone of about 1 hour, and/or an area under the plasma concentration curve (AUC) extrapolated to infinity (AUC(0-inf)) of 85 to 100 hr-ng/mL.

18. The method of claim 12, wherein the disease or disorder is selected from the group consisting of obesity, anorexia, bulimia, depression, major depressive disorder (MDD), acute depression, post-traumatic depression, anxiety, acute anxiety, panic disorders, phobias, social anxiety disorder, social withdrawal, psychosis, acute psychosis, schizophrenia, positive and/or negative symptoms of schizophrenia, obsessive-compulsive disorder, migraine, attention deficit disorder, attention deficit hyperactivity disorder, sleep disorders, anger disorders, agitation, dementia, Alzheimer's disease, Parkinson's dementia, bipolar disorder, bipolar depression, and behavioral disturbances associated with autism.

19. The method of claim 18, wherein the disease or disorder is selected from the group consisting of depression, major depressive disorder (MDD), schizophrenia, negative symptoms of schizophrenia, bipolar disorder, and bipolar depression.

20. The capsule of claim 1, wherein the capsule comprises about 60 mg of lumateperone mono-tosylate in solid crystal form and administration of an oral dose of a single capsule under fasting conditions provides one or more of the following plasma metabolite values:
   (a) a mean Cmax for Metabolite A of 25-38 ng/ml;
   (b) a mean Cmax for Metabolite B of 16-25 ng/ml;
   (c) a mean Cmax for Metabolite C of 16-25 ng/ml;
   (d) a mean Cmax for Metabolite E of 8-13 ng/ml;
   (e) a mean Cmax for Metabolite F of 16-25 ng/ml;
   (f) a mean AUC(0-inf) for Metabolite A of 270-410 hr-ng/ml;
   (g) a mean AUC(0-inf) for Metabolite B of 43-65 hr-ng/mL;
   (h) a mean AUC(0-inf) for Metabolite C of 220-335 hr-ng/ml;
   (i) a mean AUC(0-inf) for Metabolite E of 45-68 hr-ng/ml;
   (j) a mean AUC(0-inf) for Metabolite F of 330-500 hr-ng/ml;
   (k) a ratio of Cmax (metabolite A)/Cmax (lumateperone) of 0.8-1.3;
   (l) a ratio of Cmax (metabolite B)/Cmax (lumateperone) of 0.5-0.8;
   (m) a ratio of Cmax (metabolite C)/Cmax (lumateperone) of 0.5-0.8;
   (n) a ratio of Cmax (metabolite E)/Cmax (lumateperone) of 0.3-0.4;
   (o) a ratio of Cmax (metabolite F)/Cmax (lumateperone) of 0.5-0.8;
   (p) a ratio of AUC(0-inf)(metabolite A)/AUC(0-inf)(lumateperone) of 3.2-4.8;
   (q) a ratio of AUC(0-inf)(metabolite B)/AUC(0-inf)(lumateperone) of 0.5-0.8;
   (r) a ratio of AUC(0-inf)(metabolite C)/AUC(0-inf)(lumateperone) of 2.6-4.0;
   (s) a ratio of AUC(0-inf)(metabolite E)/AUC(0-inf)(lumateperone) of 0.5-0.8; and/or
   (t) a ratio of AUC(0-inf)(metabolite F)/AUC(0-inf)(lumateperone) of 3.9-6.0;
   wherein metabolites A, B, C, E, and F, are defined as follows:

Metabolite A

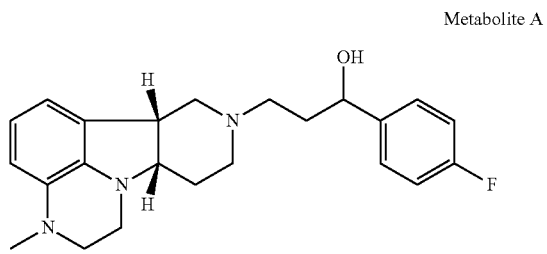

Metabolite C

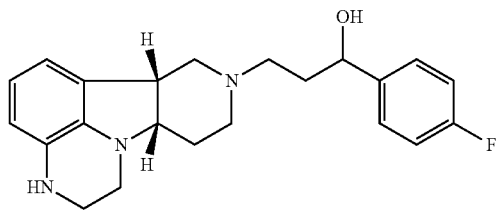

Metabolite B

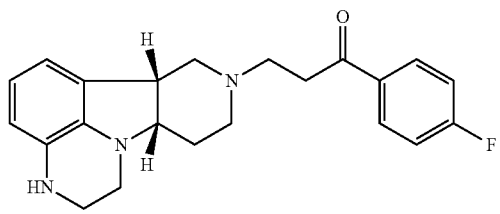

Metabolite F

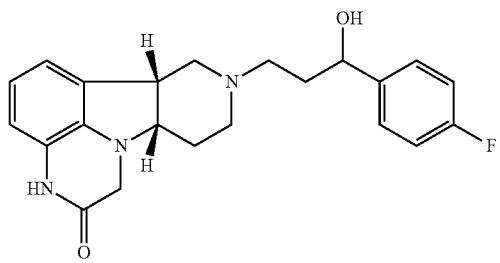

Metabolite E

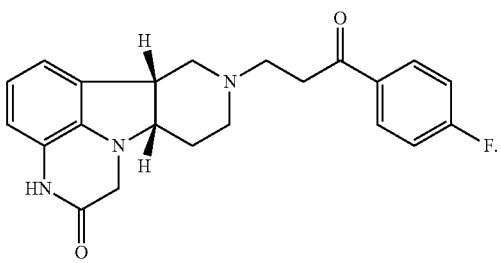

21. The capsule of claim 1, wherein administration of an oral dose of a single capsule under fasting conditions provides a maximal plasma concentration of lumateperone of 15-55 ng/mL.

22. The capsule of claim 1, wherein administration of an oral dose of a single capsule under fasting conditions provides a time to maximal plasma concentration of lumateperone of 0.7 to 1.5 hours.

23. The capsule of claim 1, wherein administration of an oral dose of a single capsule under fasting conditions an area under the plasma concentration curve (AUC) extrapolated to infinity (AUC(0-inf)) of 51 to 135 hours-ng/mL.

24. The capsule of claim 1, wherein administration of an oral dose of a single capsule under fasting conditions provides a mean maximal plasma concentration (Cmax) of lumateperone of 30-40 ng/mL.

25. The capsule of claim 1, wherein administration of an oral dose of a single capsule under fasting conditions provides a mean time to maximal plasma concentration (Tmax) of lumateperone of 1-1.2 hours.

26. The capsule of claim 1, wherein administration of an oral dose of a single capsule under fasting conditions provides an area under the plasma concentration curve (AUC) extrapolated to infinity (AUC(0-inf)) of 70 to 115 hr-ng/mL.

27. The capsule of claim 1, wherein administration of an oral dose of a single capsule under fasting conditions provides a mean time to maximal plasma concentration (Tmax) of lumateperone of about 1 hour.

28. The capsule of claim 1, wherein administration of an oral dose of a single capsule under fasting conditions provides an area under the plasma concentration curve (AUC) extrapolated to infinity (AUC(0-inf)) of 85 to 100 hr-ng/mL.

\* \* \* \* \*